US012723088B2

(12) United States Patent
Chin et al.

(10) Patent No.: US 12,723,088 B2
(45) Date of Patent: Sep. 1, 2026

(54) ANTIGEN BINDING MOLECULES AND METHODS THEREOF II

(71) Applicant: Agency for Science, Technology and Research, Singapore (SG)

(72) Inventors: Chui Ping Angela Chin, Singapore (SG); Boon Hwa Andre Choo, Singapore (SG); Wey Jia Fong, Singapore (SG); Mei Yee Vanessa Ding, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 470 days.

(21) Appl. No.: 18/275,519

(22) PCT Filed: Jan. 28, 2022

(86) PCT No.: PCT/SG2022/050043
§ 371 (c)(1),
(2) Date: Aug. 2, 2023

(87) PCT Pub. No.: WO2022/169416
PCT Pub. Date: Aug. 11, 2022

(65) Prior Publication Data

US 2024/0132595 A1 Apr. 25, 2024

(30) Foreign Application Priority Data

Feb. 3, 2021 (SG) ............................ 10202101165S

(51) Int. Cl.
*C07K 16/28* (2006.01)
*A61K 47/68* (2017.01)
*A61P 35/00* (2006.01)

(52) U.S. Cl.
CPC .... *C07K 16/2833* (2013.01); *A61K 47/68031* (2023.08); *A61P 35/00* (2018.01); *C07K 2317/24* (2013.01); *C07K 2317/565* (2013.01)

(58) Field of Classification Search
CPC ............ C07K 16/2833; C07K 2317/24; C07K 2317/565; C07K 16/3061; A61K 47/68031; A61K 47/6849; A61K 47/6867; A61K 47/6877; A61K 2039/545; A61P 35/00
See application file for complete search history.

(56) References Cited

U.S. PATENT DOCUMENTS

2019/0144560 A1 5/2019 Miazek et al.

FOREIGN PATENT DOCUMENTS

JP 2019-85376 A 6/2019
WO WO-2017151000 A1 * 9/2017 ............. A61P 35/02

OTHER PUBLICATIONS

Graves S. S. & Storb R., "Developments and translational relevance for the canine haematopoietic cell transplantation preclinical model," *Veterinary and Comparative Oncology*, May 9, 2020, vol. 18, No. 4, pp. 471-483.
Miyamae J. et al., "Identification of novel polymorphisms and two distinct haplotype structures in dog leukocyte antigen class I genes: DLA-88, DLA-12 and DLA-64," *Immunogenetics*, Sep. 27, 2017, vol. 70, No. 4, pp. 237-255.
International Search Report (ISR) received in corresponding International Application No. PCT/SG2022/050043, mailed Mar. 18, 2022, 5 pages.
International Preliminary Report on Patentability (IPRP) received in corresponding International Application No. PCT/SG2022/050043, issued Aug. 3, 2023, 7 pages.
Lisowska, M. et al., "Development of novel monoclonal antibodies to dog leukocyte antigen DR displaying direct and immune-mediated cytotoxicity toward canine lymphoma cell lines," Hematological Oncology, 36:554-560, Mar. 24, 2018.
Miyamae, J. et al., "Large-Scale Polymorphism Analysis of Dog Leukocyte Antigen Class I and Class II Genes (DLA-88, DLA-12/88L and DLA-DRB1) and Comparison of the Haplotype Diversity between Breeds in Japan," Cells, 12(5):809, Mar. 6, 2023.
Steplewski, Z. et al., "Canine lymphoma-associated antigens defined by murine monoclonal antibodies," Cancer Immunology Immunotherapy, 24(3): 197-201, Jan. 1, 1987.

* cited by examiner

*Primary Examiner* — Sean E Aeder
*Assistant Examiner* — Yie Chia Lee
(74) *Attorney, Agent, or Firm* — Kilpatrick Townsend & Stockton LLP

(57) ABSTRACT

The invention relates to antigen-binding molecules that specifically bind to MHC Class I DLA-12 antigen. In one embodiment, the antigen-binding molecule is an antibody that specifically binds to canine MHC Class I DLA-12 antigen. Chimeric molecules of the antibody conjugated to another heterologous moiety are also provided. In one embodiment, the heterologous moiety is monomethyl auristatin E (MMAE). A method of inhibiting cancer using the antibody or the chimeric molecule thereof is also provided. In another embodiment, the antibody-MMAE conjugate suppresses tumour development in a murine model of B cell lymphoma.

14 Claims, 18 Drawing Sheets

Specification includes a Sequence Listing.

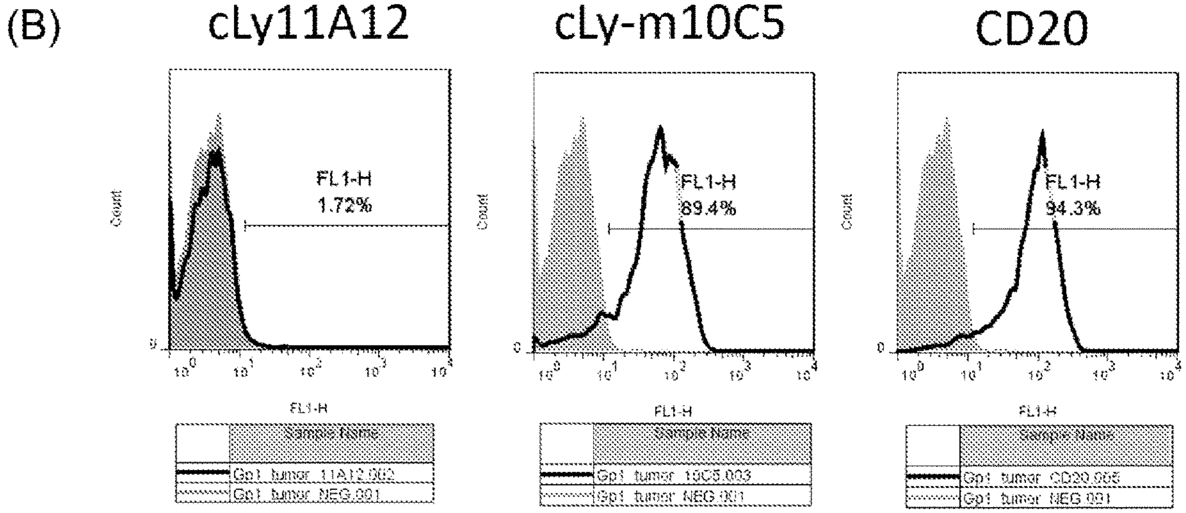
Figure 12(B) (end)

(B)
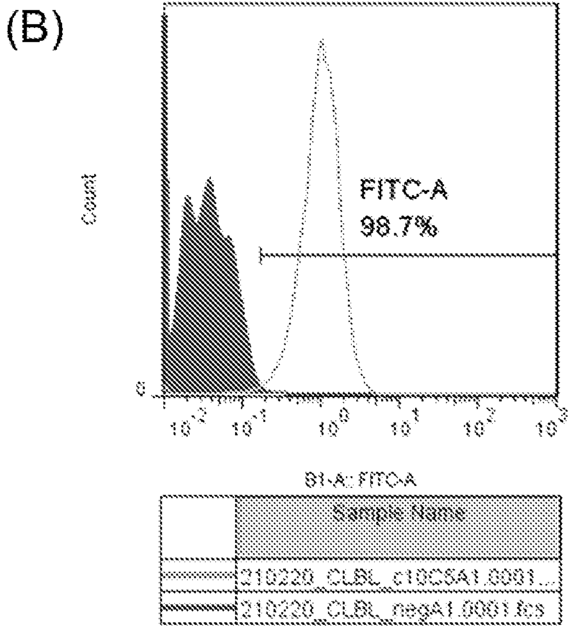
Figure 14(B) (end)

(A)

(B)

ANTIGEN BINDING MOLECULES AND METHODS THEREOF II

CROSS-REFERENCE TO RELATED APPLICATIONS

The present application is a § 371 National Phase Application of International Application No. PCT/SG2022/050043, filed Jan. 28, 2022, which application claims the benefit of Singapore Patent Application No. 10202101165S, filed Feb. 3, 2021, the contents of which are incorporated by reference in their entireties for all purposes herein.

FIELD OF INVENTION

The invention relates generally to antigen-binding molecules. In particular, the present disclosure relates to antigen-binding molecules that specifically bind to MHC Class I DLA-12 antigen.

BACKGROUND

Cancer in companion animals is a key concern for both veterinarians and pet owners as it is a major diagnosis as well as leading cause of death in 47% of the dogs and 32% of the cats. Some common types of cancer in companion animals include skin, lymphoma, hemangiosarcoma and mammary cancer. Despite the willingness of pet owners to pay and pursue treatments, cancer therapies for companion animals remain challenging due to lack of targeted oncology drugs for animal use.

Lymphoma is one of the most common cancer type in dogs and cats, along with Mast Cells tumours, Hemangiosarcoma, Melanoma, Osteosarcoma and Mammary Carcinoma. The average survival time without treatment for the most common type of lymphoma is 4 to 6 weeks. The current recommended treatment for lymphoma involves CHOP multidrug chemotherapy: cyclophosphamide, hydroxydaunorubicin (doxorubicin), Oncovin® (vincristine), and prednisone. However, it is uncommon for dogs to be cured of lymphoma although remission can be achieved. Furthermore, reoccurrence of the disease is usually observed within a year post-treatment, with less than 25% of dogs surviving two years.

Although there are moderate overall response post treatments, side effects exist which sometimes resulted in fatal complications. Due to the toxicity of the chemotherapeutic drugs, pet owners handling dogs undergoing treatment have to be protected with chemotherapy-resistant gloves to avoid contact with its faeces, urine, vomit, and saliva.

Accordingly, it is generally desirable to overcome or ameliorate one or more of the above mentioned difficulties.

SUMMARY

Disclosed herein is an antigen-binding molecule that specifically binds to MHC Class I DLA-12 antigen.

Disclosed herein is a chimeric molecule comprising an antigen-binding molecule as defined herein and a heterologous moiety.

Disclosed herein is an isolated polynucleotide comprising a nucleic acid sequence encoding the antigen-binding molecule or the chimeric molecule as defined herein.

Disclosed herein is a construct comprising a polynucleotide as defined herein in operable connection with one or more control sequences.

Disclosed herein is a host cell that contains the construct as defined herein.

Disclosed herein is a pharmaceutical composition comprising an antigen-binding molecule or a chimeric molecule as defined herein Disclosed herein is an antigen-binding molecule, a chimeric molecule or a pharmaceutical composition as defined herein for use as a medicament.

Disclosed herein is a method for reducing or inhibiting proliferation and/or viability of a cancer cell, the method comprising contacting the cancer cell with a therapeutically effective amount of an antigen-binding molecule, a chimeric molecule or a pharmaceutical composition as defined herein.

Disclosed herein is a method of reducing or inhibiting proliferation, survival and/or viability of a cancer cell in a subject, the method comprising administering a therapeutically effective amount of an antigen-binding molecule, a chimeric molecule or a pharmaceutical composition as defined herein to the subject.

Disclosed herein is a method of treating a cancer in a subject, the method comprising administering a therapeutically effective amount of an antigen-binding molecule, a chimeric molecule or a pharmaceutical composition as defined herein to the subject.

Disclosed herein is a method of treating a disease or condition associated with an undesired expression of MHC Class I DLA-12 antigen in a subject, wherein the method comprises administering a therapeutically effective amount of an antigen-binding molecule, a chimeric molecule or a pharmaceutical composition as defined herein to the subject.

Disclosed herein is a method of detecting the likelihood of the presence of a cancer in a subject, the method comprising determining the level of MHC Class I DLA-12 antigen in a sample obtained from the subject, wherein an increased level of MHC Class I DLA-12 antigen as compared to a reference indicates the likelihood of the presence of a cancer in the subject.

BRIEF DESCRIPTION OF THE FIGURES

FIG. 14. Characterization of tumours formed in mice treated with PBS (negative control). (A) Tumours formed were well-vascularized (B) Tumours formed expressed antigens that cLy-c10C5 binds to.

DETAILED DESCRIPTION

Figure 1:
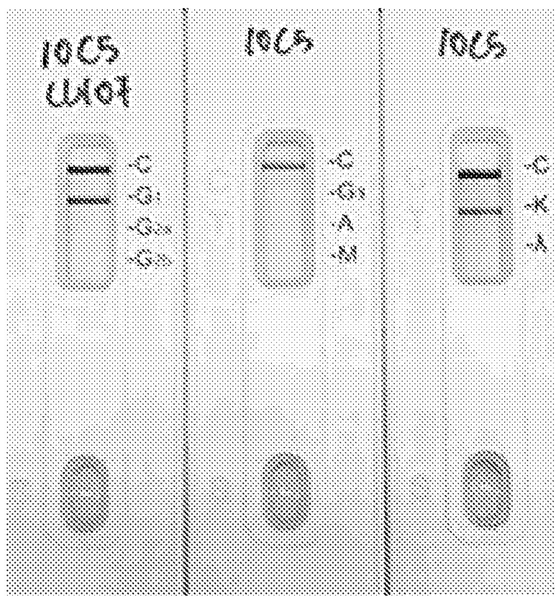
FIG. 1. Isotype of mAb cLy-m10C5 (antibody of clone 10C5 with mouse constant regions) is IgG1.

The present disclosure teaches antigen-binding molecules that specifically bind to MHC Class I DLA-12 antigen.

Disclosed herein is an antigen-binding molecule that specifically binds to MHC Class I DLA-12 antigen.

Without being bound by theory, is the inventors have developed a chimeric (canine constant region genes-mouse variable region genes) IgGb mAb to target B cell lymphoma. The antibody binds to an antigen present on the cell surface of B cell lymphoma, Mast cancer cells and tissues from the respective xenografts. It has low reactivity to normal canine cells and tissues, with the exception of PBMCs. Several characterization assays were performed to determine the identity of the antigen target. When the antibody was conjugated to a toxin such as MMAE, it demonstrated highly-specific cytotoxicity. Tumor regression was achieved in immunocompromised mice when treated with the MMAE conjugated antibody.

In one embodiment, the antigen-binding molecule binds specifically to canine MHC Class I DLA-12 antigen. The canine MHC Class I DLA-12 antigen may have a protein accession number of 046880.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity. Representative antigen-binding molecules that are useful in the practice of the present invention include antibodies and their antigen-binding fragments. The term "antigen-binding molecule" includes antibodies and antigen-binding fragments of antibodies.

In an embodiment, the antigen-binding molecule, as described herein, is conjugated to another molecule or moiety, including functional moieties (e.g., toxins), detectable moieties (e.g., fluorescent molecules, radioisotopes), small molecule drugs and polypeptides.

The term "antibody", as used herein, is understood to mean any antigen-binding molecule or molecular complex comprising at least one complementarity determining region (CDR) that binds specifically to, or interacts specifically with, the target antigen. The term "antibody" includes full-length immunoglobulin molecules comprising two heavy (H) chains and two light (L) chains inter-connected by disulfide bonds, as well as multimers thereof (e.g., IgM). Each heavy chain comprises a heavy chain variable region (which may be abbreviated as HCVR, VH or $V_H$) and a heavy chain constant region. The heavy chain constant region typically comprises three domains—$C_H1$, $C_H2$ and $C_H3$. Each light chain comprises a light chain variable region (which may be abbreviated as LCVR, VL, VK, $V_K$ or $V_L$) and a light chain constant region. The light chain constant region will typically comprise one domain ($C_L1$).

The $V_H$ and $V_L$ regions can be further subdivided into regions of hypervariability, termed complementarity determining regions (CDRs), interspersed with regions that are more conserved, also referred to as framework regions (FR). Each $V_H$ and $V_L$ typically comprises three CDRs and four FRs, arranged from amino-terminus to carboxy-terminus in the following order: FR1, CDR1, FR2, CDR2, FR3, CDR3, FR4. In some embodiments, the FRs of the antigen-binding molecules described herein may be identical to the FR of germline sequences of the target species (i.e., the species to which the antigen-binding molecules or antigen-binding fragments thereof, as described herein, will be administered). In some embodiments, the FR may be naturally or artificially modified. Whilst it is generally desirable that each of the FR sequences are identical to FR sequences derived from immunoglobulin molecules of the target species, including to minimize an immune response being raised against the binding molecule upon administration to a subject of the target species, in some embodiments, the antigen-binding molecule, or antigen-binding fragment thereof, may comprise one or more amino acid residues across one or more of its FR sequences that would be foreign at a corresponding position in one or more FR from the target species.

An antibody includes an antibody of any class, such as IgG, IgA, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called α, δ, ε, γ, and p, respectively. The subunit structures and three-dimensional configurations of different classes of immunoglobulins are well known to a person skilled in the art.

As used herein, the term "complementarity determining regions" (CDRs; i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined for example by Kabat (i.e., about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e., about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some instances, a complementarity determining region can include amino acids from both a CDR region defined according to Kabat and a hypervariable loop.

An "antigen-binding site" refers to the site, i.e., one or more amino acid residues, of an antigen binding molecule which provides interaction with the antigen. For example, the antigen binding site of an antibody comprises amino acid residues from the complementarity determining regions (CDRs). A native immunoglobulin molecule typically has two antigen binding sites, a Fab molecule typically has a single antigen binding site. An antigen-binding site of an antigen-binding molecule described herein typically binds specifically to an antigen and more particularly to an epitope of the antigen.

The present disclosure also extends to antigen-binding molecules that bind specifically to MHC Class I DLA-12 in dogs or its equivalent in any species. The antigen may be the human equivalent of MHC Class I DLA-12 (otherwise known as HLAA) or canine MHC Class I DLA-12. In an embodiment, the antigen is canine MHC Class I DLA-12. In another embodiment, the antigen is human MHC Class I DLA-12 (or HLAA). The present disclosure extends to antigen binding molecules that bind specifically to native DLA-12 (i.e., naturally-occurring DLA-12), as well as to variants thereof. Such variants may include DLA-12 molecules that differ from a naturally-occurring (wild-type) molecule by one or more amino acid substitutions, deletions and/or insertions. Variant DLA-12 molecules of this type may be naturally-occurring or synthetic (e.g., recombinant) forms. It is to be understood, however, that in one embodiment, the antigen-binding molecules described herein bind specifically to a native form of DLA-12, whether of a human or non-human species (such as canine DLA-12).

The terms "antigen-binding fragment", "antigen-binding portion", "antigen-binding domain" and "antigen-binding site" are used interchangeably herein to refer to a part of an antigen-binding molecule that participates in antigen-binding. These terms include any naturally occurring, enzymatically obtainable, synthetic, or genetically engineered polypeptide or glycoprotein that specifically binds an antigen to form a complex.

Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, one-armed antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment" as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$, (vi) $V_H$-$C_H2$-$C_H3$; (vii) $V_H$-$C_L$; (viii) $V_L$-$C_H1$; (ix) $V_L$-$C_H2$, (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)). A multispecific antigen-binding molecule will typically comprise at least two different variable domains, wherein each variable domain is capable of specifically binding to a separate antigen or to a different epitope on the same antigen. Any multispecific antigen-binding molecule format, including bispecific antigen-binding molecule formats, may be adapted for use in the context of an antigen-binding fragment of an antibody of the present disclosure using routine techniques available in the art.

The term "variable region" or "variable domain" refers to the domain of an antibody heavy or light chain that is involved in binding the antigen binding molecule to antigen. The variable domains of the heavy chain and light chain ($V_H$ and $V_L$, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single $V_H$ or $V_L$ domain may be sufficient to confer antigen-binding specificity.

The term "constant domains" or "constant region" as used herein denotes the sum of the domains of an antibody other than the variable region. The constant region is not directly involved in binding of an antigen, but exhibits various immune effector functions.

In one embodiment, the antigen-binding molecule or antigen-binding fragment thereof is modified for compatibility with the target species. Thus, in an embodiment, the antigen-binding molecule or antigen-binding fragment thereof is humanized or caninized.

By "humanized" is meant that the antigen-binding molecule comprises an amino acid sequence that is compatible with humans, such that the amino acid sequence is unlikely to be seen as foreign by the immune system of a human subject. In an embodiment, the humanized antigen-binding molecule comprises one or more immunoglobulin framework regions derived from one or more human immunoglobulin molecules. In some embodiments, all of the framework regions of the humanized antigen-binding molecule will be derived from one or more human immunoglobulin molecules. The humanized antibody may optionally comprise an immunoglobulin heavy chain constant region derived from a human immunoglobulin molecule.

By "caninized" is meant that the antigen-binding molecule comprises an amino acid sequence that is compatible with canine, such that the amino acid sequence is unlikely to be seen as foreign by the immune system of a canine subject. In an embodiment, the caninized antigen-binding molecule comprises one or more immunoglobulin framework regions derived from one or more canine immunoglobulin molecules. In some embodiments, all of the framework regions of the caninized antigen-binding molecule will be derived from one or more canine immunoglobulin molecules. The caninized antibody may optionally comprise an immunoglobulin heavy chain constant region derived from a canine immunoglobulin molecule.

It is to be understood that the present disclosure also extends to antigen-binding molecules that are compatible with species other than human and canine. In this context, the antigen-binding molecules can be referred to as "speciesized", referring to the target species to which the molecule will be administered.

The phrase "specifically binds" or "specific binding" refers to a binding reaction between two molecules that is at least two times the background and more typically more than 10 to 100 times background molecular associations under physiological conditions. When using one or more detectable binding agents that are proteins, specific binding is determinative of the presence of the protein, in a heterogeneous population of proteins and other biologics. Thus, under designated immunoassay conditions, the specified antigen-binding molecule binds to a particular antigenic determinant, thereby identifying its presence. Specific binding to an antigenic determinant under such conditions requires an antigen-binding molecule that is selected for its specificity to that determinant. This selection may be achieved by subtracting out antigen-binding molecules that cross-react with other molecules. A variety of immunoassay formats may be used to select antigen-binding molecules (e.g., immunoglobulins) such that they are specifically immunoreactive with a particular antigen. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity). Methods of determining binding affinity and specificity are also well known in the art (see, for example, Harlow and Lane, supra); Friefelder, "Physical Biochemistry: Applications to biochemistry and molecular biology" (W.H. Freeman and Co. 1976)).

"Affinity" or "binding affinity" refers to the strength of the sum total of non-covalent interactions between a single binding site of a molecule (e.g., an antigen-binding molecule) and its binding partner (e.g., an antigen). Unless indicated otherwise, as used herein, "binding affinity" refers to intrinsic binding affinity which reflects a 1:1 interaction between members of a binding pair e.g., an antigen-binding molecule. The affinity of a molecule X for its partner Y can generally be represented by the dissociation constant (Kd), which is the ratio of dissociation and association rate constants ($k_{off}$ and $k_{on}$, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

The terms "polypeptide", "peptide", or "protein" are used interchangeably herein to designate a linear series of amino acid residues connected one to the other by peptide bonds between the alpha-amino and carboxy groups of adjacent residues. The amino acid residues are usually in the natural "L" isomeric form. However, residues in the "D" isomeric form can be substituted for any L-amino acid residue, as long as the desired functional property is retained by the polypeptide As used herein, the term "modified antibody" includes synthetic forms of antibodies which are altered such that they are not naturally occurring, e.g., antibodies that comprise at least two heavy chain portions but not two complete heavy chains (such as domain deleted antibodies or minibodies); multispecific forms of antibodies (e.g., bispecific, trispecific, etc.) altered to bind to two or more different antigens or to different epitopes on a single antigen; heavy chain molecules joined to scFv molecules and the like. ScFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen).

The antigen-binding molecule may comprise a) a heavy chain variable (VH) region comprising the VHCDR1 amino acid sequence K A S G Y T F T D Y N M H (SEQ ID NO: 1), the VHCDR2 amino acid sequence Y I Y P Y N G G T D Y N Q K F K (SEQ ID NO: 2) and the VHCDR3 amino acid sequence G G L V G A M D Y (SEQ ID NO: 3). The antigen-binding molecule may comprise a light chain variable (VL) region comprising the VLCDR1 amino acid sequence R A S G N I H N S L A (SEQ ID NO: 4), the VLCDR2 amino acid sequence N A K T L P D (SEQ ID NO: 5) and the VLCDR3 amino acid sequence Q H F W S I P W T (SEQ ID NO: 6).

In one embodiment, the antigen-binding molecule comprises:

a) a heavy chain variable (VH) region comprising the VHCDR1 amino acid sequence K A S G Y T F T D Y N M H (SEQ ID NO: 1), the VHCDR2 amino acid sequence Y I Y P Y N G G T D Y N Q K F K (SEQ ID NO: 2) and the VHCDR3 amino acid sequence G G L V G A M D Y (SEQ ID NO: 3); and b) a light chain variable (VL) region comprising the VLCDR1 amino acid sequence R A S G N I H N S L A (SEQ ID NO: 4), the VLCDR2 amino acid sequence N A K T L P D (SEQ ID NO: 5) and the VLCDR3 amino acid sequence Q H F W S I P W T (SEQ ID NO: 6).

The antigen-binding molecule may comprise:

a) a VH region comprising an amino acid sequence having at least 70% (including at least 71% to 99% and all integer percentages therebetween) sequence identity to:

```
                                   (SEQ ID NO: 7)
E V Q L Q Q S G P E L V K P G A S V K I
S C K A S G Y T F T D Y N M H W V K Q S
H G K S L E W I G Y I Y P Y N G G T D Y
N Q K F K S K A T L T V D N S S S T A Y
```

-continued

```
M E L R S L T S D D S T V Y Y C A R G G
L V G A M D Y W G Q G T S V T V S S.
```

The antigen-binding molecule may comprise b) a VL region comprising an amino acid sequence having at least 70% (including at least 71% to 99% and all integer percentages therebetween) sequence identity to:

```
                                   (SEQ ID NO: 8)
D I Q M T Q S P A S L S A S V G E T V T
I T C R A S G N I H N S L A W Y Q Q K Q
G K S P Q L L V Y N A K T L P D G V P S
R F S G S G S G T Q Y S L K I N S L Q P
E D F G S Y Y C Q H F W S I P W T F G G
G T K L E I K.
```

In one embodiment, the antigen-binding molecule comprises:

a) a VH region comprising an amino acid sequence having at least 70% (including at least 71% to 99% and all integer percentages therebetween) sequence identity to:

```
                                          (SEQ ID NO: 7)
E V Q L Q Q S G P E L V K P G A S V K I S C K A S
G Y T F T D Y N M H W V K Q S H G K S L E W I G Y
I Y P Y N G G T D Y N Q K F K S K A T L T V D N S
S S T A Y M E L R S L T S D D S T V Y Y C A R G G
L V G A M D Y W G Q G T S V T V S S;
```
and b) a VL region comprising an amino acid sequence having at least 70% (including at least 71% to 99% and all integer percentages therebetween) sequence identity to:

```
                                   (SEQ ID NO: 8)
D I Q M T Q S P A S L S A S V G E T V T
I T C R A S G N I H N S L A W Y Q Q K Q
G K S P Q L L V Y N A K T L P D G V P S
R F S G S G S G T Q Y S L K I N S L Q P
E D F G S Y Y C Q H F W S I P W T F G G
G T K L E I K.
```

In one embodiment, the antigen-binding molecule comprises a) a heavy chain variable region (VH) as defined herein comprising at least 70% sequence identity to at least one region other than a CDR of the VH amino acid sequence set forth in SEQ ID NO:7 (e.g., to at least one framework region, such as 1, 2, 3 or 4 framework regions, of the VH), and b) a light chain variable region (VL) as defined herein comprising at least 70% sequence identity to at least one region other than a CDR of the VL amino acid sequence set forth in SEQ ID NO:8 (e.g., to at least one framework region, such as 1, 2, 3 or 4 framework regions, of the VL).

In one embodiment, the antigen-binding molecule comprises a) a VH as defined herein which is distinguished from the VH amino acid sequence set forth in SEQ ID NO:7 by a deletion, substitution or addition of one or more (e.g., 1, 2, 3, 4 or 5) amino acids in at least one region other than a CDR of the VH amino acid sequence set forth in SEQ ID NO:7 (e.g., in at least one framework region, such as in 1, 2, 3 or 4 framework regions, of the VH), and b) a VL as defined in (1) which is distinguished from the VL amino acid sequence set forth in SEQ ID NO:8 by a deletion, substitution or addition of one or more (e.g., 1, 2, 3, 4 or 5) amino acids in at least one region other than a CDR of the VL amino acid sequence set forth in SEQ ID NO:8 (e.g., in at least one framework region, such as in 1, 2, 3 or 4 framework regions, of the VL).

The antigen-binding molecule may comprise a canine IgGB constant region. The antigen-binding molecule may comprise a heavy chain constant region comprising an amino acid sequence having at least 70% (or at least 75%, 80%, 85%, 90% or 95%) sequence identity to:

```
                                         (SEQ ID NO: 9)
TTAPSVFPLAPSCGSTSGSTVALACLVSGYFPEPVTVSWNSGSLTSGVHT

FPSVLQSSGLYSLSSMVTVPSSRWPSETFTCNVAHPASKTKVDKPVPKRE

NGRVPRPPDCPKCPAPEMLGGPSVFIFPPKPKDTLLIARTPEVTCVVVDL

DPEDPEVQISWFVDGKQMQTAKTQPREEQFNGTYRVVSVLPIGHQDWLKG

KQFTCKVNNKALPSPIERTISKARGQAHQPSVYVLPPSREELSKNTVSLT

CLIKDFFPPDIDVEWQSNGQQEPESKYRTTPPQLDEDGSYFLYSKLSVDK

SRWQRGDTFICAVMHEALHNHYTQESLSHSPGK.
```

The antigen-binding molecule may comprise a light chain constant region comprising an amino acid sequence having at least 70% (or at least 75%, 80%, 85%, 90% or 95%) sequence identity to:

```
                                        (SEQ ID NO: 10)
DAQPAVYLFQPSPDQLHTGSASVVCLLNSFYPKDINVKWKVDGVIQDTGI

QESVTEQDKDSTYSLSSTLTMSSTEYLSHELYSCEITHKSLPSTLIKSFQ

RSECQRVD.
```

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G and I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

The antigen-binding molecule as defined herein may comprise one or more conservative amino acid substitutions.

A "conservative amino acid substitution" is to be understood as meaning a substitution in which the amino acid residue is replaced with an amino acid residue having a similar side chain. Families of amino acid residues having similar side chains have been defined in the art, which can be generally sub-classified as shown in the table "Amino Acid Classification", below:

Amino Acid Sub-Classification

| Sub-classes | Amino acids |
|---|---|
| Acidic | Aspartic acid, Glutamic acid |
| Basic | Noncyclic: Arginine, Lysine; Cyclic: Histidine |
| Charged | Aspartic acid, Glutamic acid, Arginine, Lysine, Histidine |
| Small | Glycine, Serine, Alanine, Threonine, Proline |
| Polar/neutral | Asparagine, Histidine, Glutamine, Cysteine, Serine, Threonine |
| Polar/large | Asparagine, Glutamine |
| Hydrophobic | Tyrosine, Valine, Isoleucine, Leucine, Methionine, Phenylalanine, Tryptophan |
| Aromatic | Tryptophan, Tyrosine, Phenylalanine |
| Residues that influence chain orientation | Glycine and Proline |

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional polypeptide can readily be determined by assaying its activity.

Conservative substitutions are also shown in the table below (EXEMPLARY AND PREFERRED AMINO ACID SUBSTITUTIONS). Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants can be screened for their ability to bind specifically to NGF using methods known to persons skilled in the art, including those methods described elsewhere herein.

Exemplary and Preferred Amino Acid Substitutions

| Original Residue | Exemplary Substitutions | Preferred Substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |

-continued

| Original Residue | Exemplary Substitutions | Preferred Substitutions |
|---|---|---|
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

The antigen-binding fragment may include recombinant, monoclonal, polyclonal, chimeric, humanised, bispecific or heteroconjugate antibodies. It may include a chimeric antigen receptor (CAR), a single variable domain, a domain antibody, antigen binding fragments, an immunologically effective fragment, a single chain Fv, a single chain antibody, a univalent antibody lacking a hinge region, a minibody, or a diabody.

In one embodiment, the antigen-binding fragment is an antibody or antigen-binding fragment thereof.

In one embodiment, the antibody or antigen binding fragment thereof is a full-length antibody, a substantially intact antibody, a Fab fragment, a scFab, a Fab', a single chain variable fragment (scFv) or a one-armed antibody.

In one embodiment, the antibody or antigen binding fragment thereof is a full-length antibody and comprises a canine constant region.

In one embodiment, the antibody or antigen-binding molecule thereof is caninized or chimerized.

Disclosed herein is a chimeric molecule comprising an antigen-binding molecule as defined herein and a heterologous moiety.

As used herein, a "chimeric" molecule is one which comprises one or more unrelated types of components or contain two or more chemically distinct regions which can be conjugated to each other, fused, linked, translated, attached via a linker, chemically synthesized, expressed from a nucleic acid sequence, etc. For example, a peptide and a nucleic acid sequence, a peptide and a detectable label, unrelated peptide sequences, and the like. In embodiments in which the chimeric molecule comprises amino acid sequences of different origin, the chimeric molecule includes (1) polypeptide sequences that are not found together in nature (i.e., at least one of the amino acid sequences is heterologous with respect to at least one of its other amino acid sequences), or (2) amino acid sequences that are not naturally adjoined. For example, a "chimeric" antibody" as used herein refers to an antibody in which a portion of the heavy and/or light chain is derived from a particular source or species, while the remainder of the heavy and/or light chain is derived from a different source or species.

In one embodiment, the heterologous moiety is a detectable moiety, a half-life extending moiety or a therapeutic moiety.

Detectable moieties contemplated by the present invention include for example any species known in the art that is appropriate for diagnostic detection, including in vitro detection and in vivo imaging. The detectable moiety may be, for example, a fluorophore, a radionuclide reporter, a metal-containing nanoparticle or microparticle, an ultrasound contrast agent (e.g., a nanobubble or microbubble) or an optical imaging dye. This also includes contrast particles visible in magnetic resonance imaging (MRI) and magnetic particle imaging (MPI). Fluorophores can be detected and/or imaged, for example, by fluorescence polarization, fluorescence-activated cell sorting and fluorescence microscopy, which may or may not be in combination with electrospray ionization-mass spectrometry (ESI-MS) detection, as well as fluorescence emission computed tomography (FLECT) imaging. Radionuclide reporters can be detected and imaged by radionuclide (nuclear) detection, such as, for example, single-photon emission computed tomography (SPECT), positron emission tomography (PET) or scintigraphic imaging. Metal-containing nanoparticles or microparticles may be detected using optical imaging, including MRI, which is typically used with paramagnetic nanoparticles or microparticles, and MPI, which is generally used with superparamagnetic particles. Ultrasound contrast agents can be detected using ultrasound imaging including contrast-enhanced ultrasound (CEU).

The detectable label may also be an enzyme-substrate label. The enzyme may generally catalyze a chemical alteration of the chromogenic substrate that can be measured using various techniques. For example, the enzyme may catalyze a chemical alteration of the chromogenic substrate that can be measured using the various techniques. For example, the example may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light that can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (RPO), alkaline phosphatase, 0-galactosidase, glucoamylase, lysozyme, saccharide oxidases (e.g., glucose oxidase, galactose oxidase, and glucose-6-phosphate dehydrogenase), heterocyclic oxidases (such as unease and xanthine oxidase), lactoperoxidase, microperoxidase, and the like.

Examples of enzyme-substrate combinations include, for example:

1) Horseradish peroxidase (HRPO) utilizes hydrogen peroxide to oxidize a dye precursor (e.g., orthophenylene diamine (OPD) or 3,3',5,5'-tetramethyl benzidine hydrochloride (TMB));
2) alkaline phosphatase (AP) with para-Nitrophenyl phosphate as chromogenic substrate; and
3) β-D-galactosidase (β-D-Gal) with a chromogenic substrate (e.g., p-nitrophenyl-β-D-galactosidase) or fluorogenic substrate 4-methylumbelliferyl-β-D-galactosidase.

In another embodiment of the invention, the antigen-binding molecule need not be labeled, and the presence thereof can be detected using a labeled antibody which binds to the antigen-binding molecule. The antigen-binding molecule of the present invention may be employed in any known assay method, such as competitive binding assays, direct and indirect sandwich assays, immunohistochemistry and immunoprecipitation assays.

In one embodiment, the chimeric molecule comprises at least one heterologous moiety that is a "half-life extending moiety". Half-life extending moieties, can comprise, for example, (i) XTEN polypeptides; (ii) Fc; (iii) albumin, (iv) albumin binding polypeptide or fatty acid, (v) the C-terminal peptide (CTP) of the 13 subunit of human chorionic gonadotropin, (vi) PAS; (vii) HAP; (viii) transferrin; (ix) polyethylene glycol (PEG); (x) hydroxyethyl starch (HES), (xi) polysialic acids (PSAs); (xii) a clearance receptor or fragment thereof which blocks binding of the chimeric molecule to a clearance receptor; (xiii) low complexity peptides; (xiv) or any combinations thereof. In some embodiments, the half-life extending moiety comprises an Fc region. In other embodiments, the half-life extending moiety comprises two Fc regions fused by a linker. Exemplary heterologous moieties also include, e.g., FcRn binding moieties (e.g., complete Fc regions or portions thereof which bind to FcRn), single chain Fc regions (scFc regions, e.g., as described in U.S. Publ. No. 20080260738, WO 2008/012543 and WO 2008/1439545), or processable scFc regions. In some embodiments, a heterologous moiety can include an attachment site for a non-polypeptide moiety such as polyethylene glycol (PEG), hydroxyethyl starch (HES), In one embodiment, the therapeutic moiety is a toxin. The toxin may, for example, be auristatin E, mertansine (DM-1), saporin, Exatecan (DX8951), gemcitabine, irinotecan, etoposide, vinblastine, pemetrexed, docetaxel, paclitaxel, platinum agents (for example, cisplatin, oxaliplatin or carboplatin), vinorelbine, capecitabine, mitoxantrone, ixabepilone, eribulin, 5-fluorouracil, trifluridine or tipiracil). The toxin may be auristatin, saporin or mertansine (DM1). In one embodiment, the toxin is Monomethyl auristatin E (MMAE). In one embodiment, the toxin is saporin. In one embodiment, the toxin is mertansine (DM1). In one embodiment, the toxin is Exatecan (DX8951).

In one embodiment, the antigen-binding molecule is joined to the therapeutic moiety via a linker. The antigen-binding molecule may be conjugated via a protease-cleavable maleimidocarproyl valine citrulline (MC-vc-PAB) linker.

In one embodiment, the antigen-binding molecule is conjugated to monomethyl auristatin E (MMAE) via a maleimidocarproyl valine citrulline (MC-vc-PAB) linker. In one embodiment, the linker-toxin combination has the chemical formula of $C_{58}H_{94}N_{10}O_{12}$ with a chemical name of L-Valinamide, N-methyl-N-[[[4-[[L-valyl-N5-(aminocarbonyl)-L-ornithyl]amino]phenyl]methoxy]carbonyl]-L-valyl-N-[(1S,2R)-4-[(2S)-2-[(1R,2R)-3-[[(1R,2S)-2-hydroxy-1-methyl-2-phenylethyl]amino]-1-methoxy-2-methyl-3-oxopropyl]-1-pyrrolidinyl]-2-methoxy-1-[(1S)-1-methylpropyl]-4-oxobutyl]-N-methyl. The conjugation may be performed by a maleimide-cysteine based method by first reducing the mAb inter-chain disulfide bonds with TCEP at 37° C. and then linking the maleimide moiety of the drug to the reduce cysteines. Drug Antibody Ratio (DAR) may be analysed on hydrophobic interaction chromatography (HIC). The DAR ratio may, for example, be between 3 and 4.

In embodiment, there is provided an antigen-binding molecule or antigen-drug conjugate (ADC) of the following formula (I):

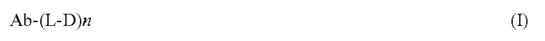

Ab-(L-D)$n$ (I)

or a pharmaceutically acceptable salt thereof, wherein

Ab is an antibody or antibody fragment thereof as defined herein:

L is a linker;

D is a cytotoxin.

In an embodiment, there is provided an ADC wherein L is a linker of the following formula (II):

(II)

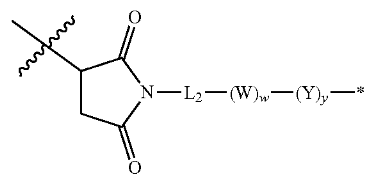

wherein

L2 is cycloalkylene-carbonyl, (C2-C6)alkyl or (C2-C6) alkyl-carbonyl;

W is an amino acid unit; w is an integer comprised of 0 to 5;

Y is PAB-carbonyl with PAB being

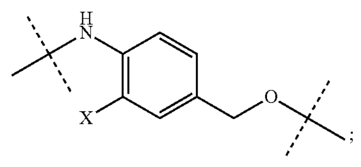

x can be H or

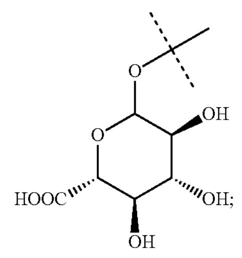

y is 0 or 1;

the asterisk indicates the point of attachment to D; and the wavy line indicates the point of attachment to Ab.

In one embodiment, there is provided an ADC wherein L2 is of the following formula:

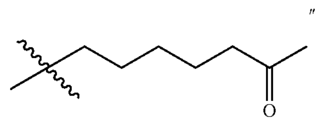 [SMILES: *CCCCCC(C)=O]

wherein the asterisk indicates the point of attachment to $(W)_w$; and the wavy line indicates the point of attachment to the nitrogen atom of the maleimide moiety of formula:

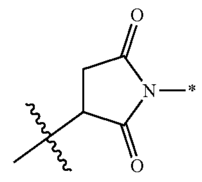 [SMILES: *C1CC(=O)N(*)C1=O]

In one embodiment, w=0, or w=2 and then (W)w is selected from:

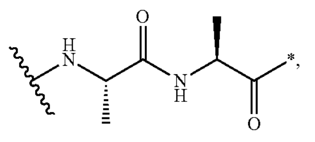
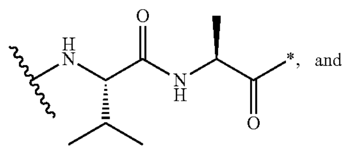
and
-continued
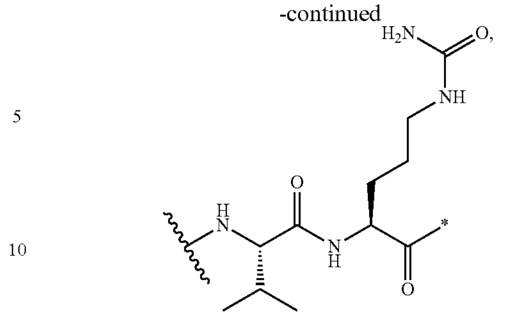
wherein
the asterisk indicates the point of attachment to $(Y)_y$; and the wavy line indicates the point of attachment to L2.
In one embodiment, there is provided an ADC wherein L is selected from:
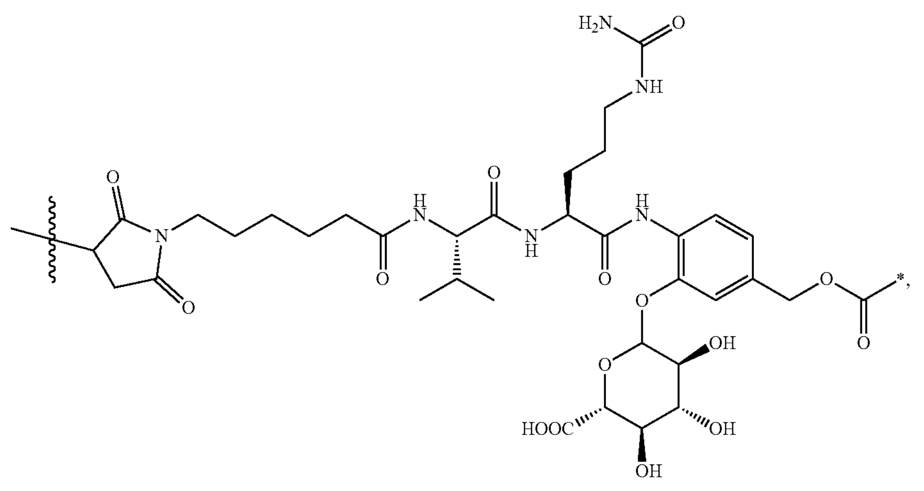
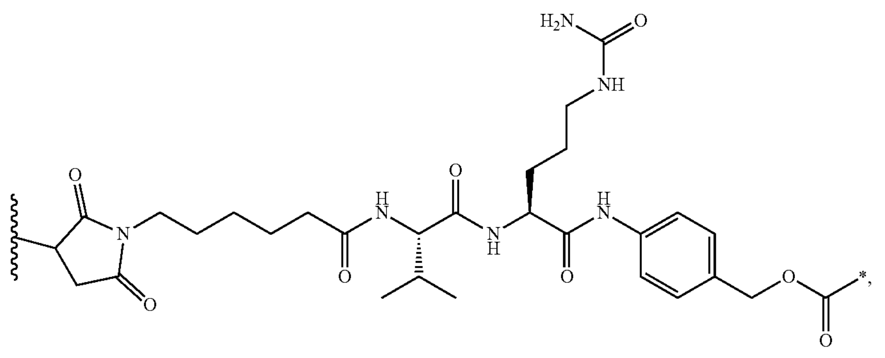

-continued

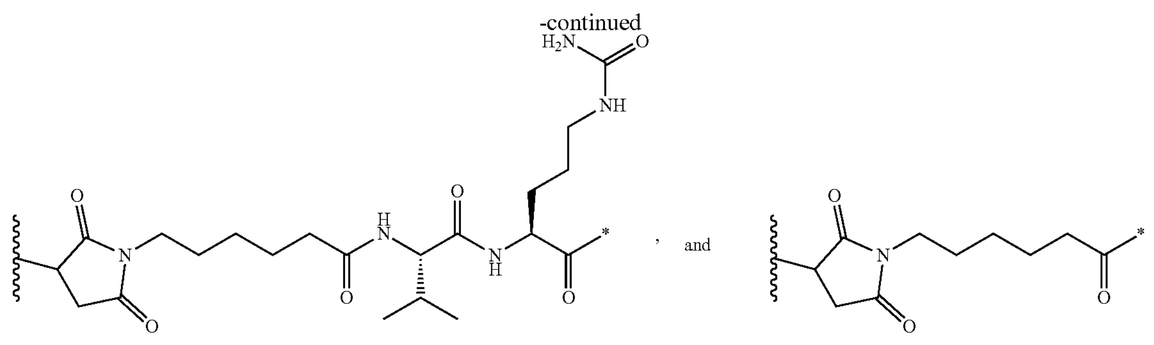

, and wherein the asterisk indicates the point of attachment to D, and the wavy line indicates the point of attachment to Ab.

In another embodiment the invention relates to an ADC wherein L is a linker of the following formula (III):

(III)

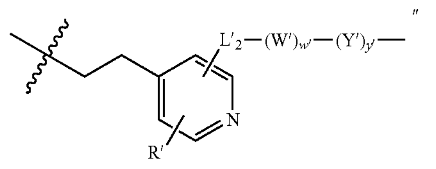

wherein

L'2 is cycloalkylene-carbonyl, (C2-C6)alkylene, or (C2-C6)alkylene-carbonyl;

W' is an amino acid unit;

w' is an integer of 0 to 5;

Y' is PAB-carbonyl with PAB being

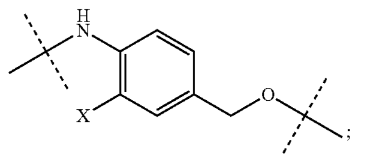

x can be H or

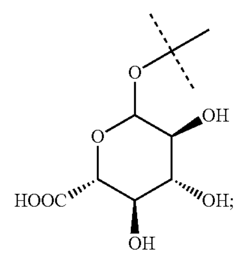

y' is 0 or 1; R' is $C_1$-$C_3$ alkenyl or H.

In an embodiment the compound of formula (III) is a compound of formula (III'):

(III')

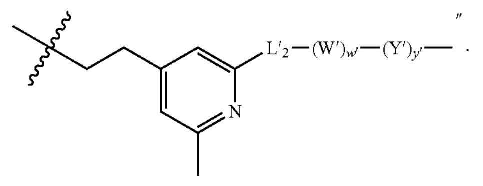

In an embodiment the compound of formula (III') is characterised with $L_2$' being $C_2$ alkylene carbonyl and w' being 2.

In an embodiment the linker compound of formula (III') is:

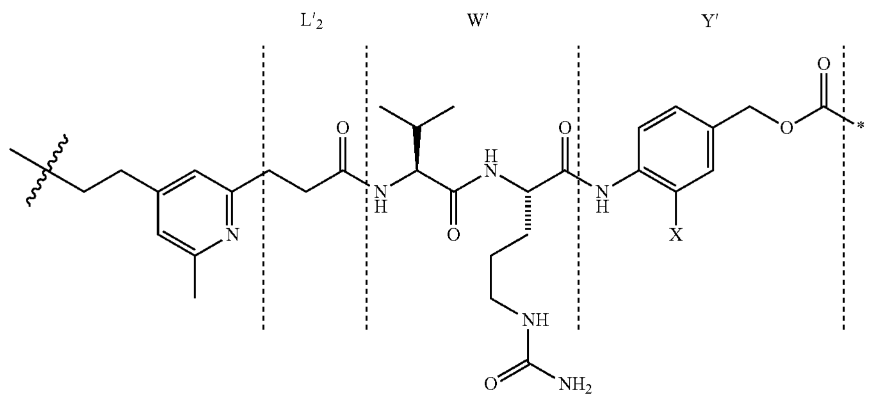

In another embodiment, the linker compound of formula (III') is:

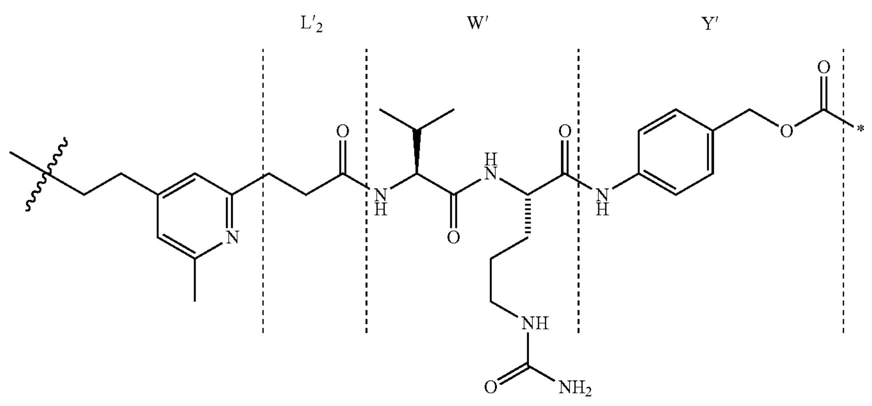 [SMILES: *CCc1cc(C)nc(CCC(=O)N[C@H](C(=O)N[C@@H](CCCNC(N)=O)C(=O)Nc2ccc(COC(*)=O)cc2)C(C)C)c1]

In another embodiment, the linker compound of formula (III') is:

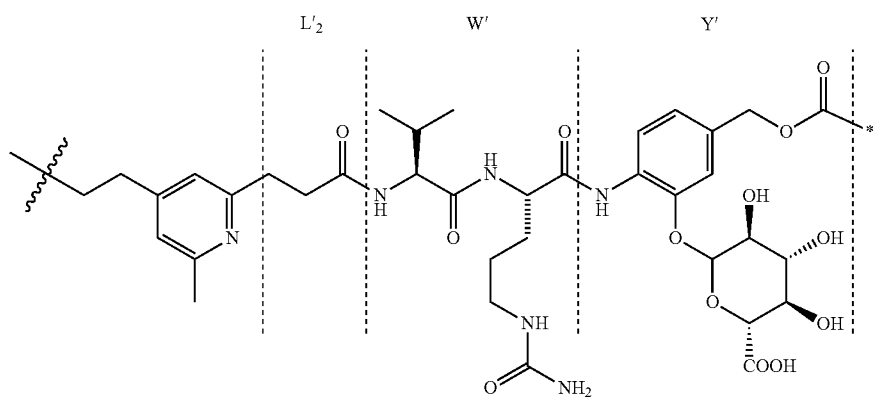 [SMILES: *CCc1cc(C)nc(CCC(=O)N[C@H](C(=O)N[C@@H](CCCNC(N)=O)C(=O)Nc2ccc(COC(*)=O)cc2OC2O[C@@H](C(=O)O)[C@H](O)[C@@H](O)[C@@H]2O)C(C)C)c1]

The present linkers may be synthesized using amide bond coupling. Many methods exist for amide synthesis. Some methods, but not limited to, are described in Montalbetti, Christian A. G. N (*Tetrahedron* 61(46), 2005, 10827-10852). Alternatively, the linkers may be synthesized using standard stepwise addition of one or more residues using, for example, a peptide or protein synthesizer. Alternatively, other methods that may be used for amide formation includes, but not limited to, Beckmann rearrangement, Schmidt reaction, Nitrile hydrolysis, Willgerodt-Kindler reaction, Passerini reaction, Ugi reaction, Bodroux reaction, Chapman rearrangement, Leuckart amide synthesis, Ritter reaction, Ester aminolysis, Schotten-Baumann reaction, ruthenium based catalysis of alcohol and amine, or Photolytic addition of formamide to olefins.

In one embodiment, the antigen-binding molecule or antigen-drug conjugate (ADC) has the following structure:

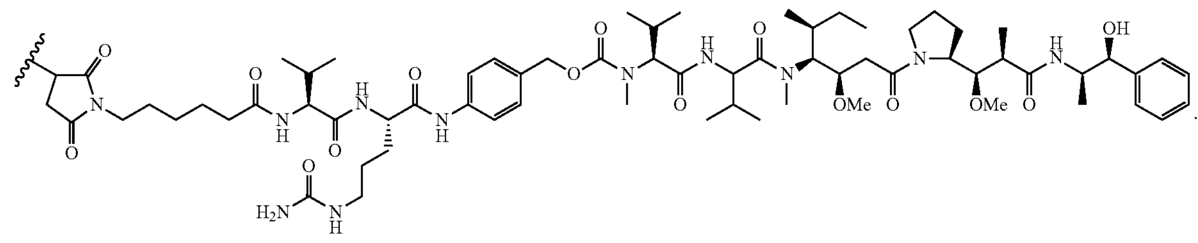

In one embodiment, the chimeric molecule is an Antibody Drug Conjugate (ADC).

In one embodiment, the antigen-binding molecule or chimeric molecule as defined herein is capable of being internalized into a cell. This makes the antigen-binding molecule or chimeric molecule suitable for delivering a therapeutic moiety into a cell.

Disclosed herein is an isolated polynucleotide comprising a nucleic acid sequence encoding the antigen-binding molecule as defined herein, or the chimeric molecule as defined herein.

The term "polynucleotide" or "nucleic acid" are used interchangeably herein to refer to a polymer of nucleotides, which can be mRNA, RNA, cRNA, cDNA or DNA. The term typically refers to polymeric form of nucleotides of at least 10 bases in length, either ribonucleotides or deoxynucleotides or a modified form of either type of nucleotide. The term includes single and double stranded forms of DNA.

Also disclosed herein is a vector that comprises a nucleic acid encoding the antigen-binding molecule as described herein.

By "vector" is meant a nucleic acid molecule, preferably a DNA molecule derived, for example, from a plasmid, bacteriophage, or virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector may also include a selection marker such as an antibiotic resistance gene that can be used for selection of suitable transformants. Examples of such resistance genes are well known to those of skill in the art.

Disclosed herein is a construct comprising a polynucleotide as defined herein in operable connection with one or more control sequences.

The term "construct" refers to a recombinant genetic molecule including one or more isolated nucleic acid sequences from different sources. Thus, constructs are chimeric molecules in which two or more nucleic acid sequences of different origin are assembled into a single nucleic acid molecule and include any construct that contains (1) nucleic acid sequences, including regulatory and coding sequences that are not found together in nature (i.e., at least one of the nucleotide sequences is heterologous with respect to at least one of its other nucleotide sequences), or (2) sequences encoding parts of functional RNA molecules or proteins not naturally adjoined, or (3) parts of promoters that are not naturally adjoined. Representative constructs include any recombinant nucleic acid molecule such as a plasmid, cosmid, virus, autonomously replicating polynucleotide molecule, phage, or linear or circular single stranded or double stranded DNA or RNA nucleic acid molecule, derived from any source, capable of genomic integration or autonomous replication, comprising a nucleic acid molecule where one or more nucleic acid molecules have been operably linked. Constructs of the present invention will generally include the necessary elements to direct expression of a nucleic acid sequence of interest that is also contained in the construct, such as, for example, a target nucleic acid sequence or a modulator nucleic acid sequence. Such elements may include control elements or regulatory sequences such as a promoter that is operably linked to (so as to direct transcription of) the nucleic acid sequence of interest, and often includes a polyadenylation sequence as well. Within certain embodiments of the invention, the construct may be contained within a vector. In addition to the components of the construct, the vector may include, for example, one or more selectable markers, one or more origins of replication, such as prokaryotic and eukaryotic origins, at least one multiple cloning site, and/or elements to facilitate stable integration of the construct into the genome of a host cell. Two or more constructs can be contained within a single nucleic acid molecule, such as a single vector, or can be containing within two or more separate nucleic acid molecules, such as two or more separate vectors. An "expression construct" generally includes at least a control sequence operably linked to a nucleotide sequence of interest. In this manner, for example, promoters in operable connection with the nucleotide sequences to be expressed are provided in expression constructs for expression in an organism or part thereof including a host cell. For the practice of the present invention, conventional compositions and methods for preparing and using constructs and host cells are well known to one skilled in the art, see for example, Molecular Cloning: A Laboratory Manual, 3rd edition Volumes 1, 2, and 3. J. F. Sambrook, D. W. Russell, and N. Irwin, Cold Spring Harbor Laboratory Press, 2000.

By "control element", "control sequence", "regulatory sequence" and the like, as used herein, mean a nucleic acid sequence (e.g., DNA) necessary for expression of an operably linked coding sequence in a particular host cell. The control sequences that are suitable for prokaryotic cells for example, include a promoter, and optionally a cis-acting sequence such as an operator sequence and a ribosome binding site. Control sequences that are suitable for eukaryotic cells include transcriptional control sequences such as promoters, polyadenylation signals, transcriptional enhancers, translational control sequences such as translational enhancers and internal ribosome binding sites (IRES), nucleic acid sequences that modulate mRNA stability, as well as targeting sequences that target a product encoded by a transcribed polynucleotide to an intracellular compartment within a cell or to the extracellular environment.

Disclosed herein is a host cell that contains the construct as defined herein.

The terms "host", "host cell", "host cell line" and "host cell culture" are used interchangeably and refer to cells into which exogenous nucleic acid has been introduced, including the progeny of such cells. Host cells include "transformants" and "transformed cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the antigen binding molecules of the present invention. Host cells include cultured cells, e.g., mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

Disclosed herein is a pharmaceutical composition comprising an antigen-binding molecule as defined herein or a chimeric molecule as defined herein.

By "pharmaceutically acceptable carrier" is meant a pharmaceutical vehicle comprised of a material that is not biologically or otherwise undesirable, i.e., the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like.

Representative pharmaceutically acceptable carriers include any and all solvents, dispersion media, coatings, surfactants, antioxidants, preservatives {e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient(s), its use in the pharmaceutical compositions is contemplated.

The pharmaceutical compositions may be in a variety of forms. These include, for example, liquid, semi-solid and solid dosage forms, such as liquid solutions (e.g., injectable and infusible solutions), dispersions or suspensions, liposomes and suppositories. The preferred form depends on the intended mode of administration and therapeutic application. Suitable pharmaceutical compositions may be administered intravenously, subcutaneously or intramuscularly. In some embodiments, the compositions are in the form of injectable or infusible solutions. A preferred mode of administration is parenteral (e.g., intravenous, subcutaneous, intraperitoneal, intramuscular). In specific embodiments, the pharmaceutical composition is administered by intravenous infusion or injection. In other embodiments, the pharmaceutical composition is administered by intramuscular or subcutaneous injection.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In the subject invention, pharmaceutically acceptable carriers include, but are not limited to, 0.01-0.1M and preferably 0.05M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition must be sterile and should be fluid to the extent that easy syringability exists. It should be stable under the conditions of manufacture and storage and will preferably be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin and/or by the maintenance of the required particle size. In specific embodiments, an agent of the present disclosure may be conjugated to a vehicle for cellular delivery. In these embodiments, the agent may be encapsulated in a suitable vehicle to either aid in the delivery of the agent to target cells, to increase the stability of the agent, or to minimize potential toxicity of the agent. As will be appreciated by a skilled artisan, a variety of vehicles are suitable for delivering an agent of the present disclosure. Non-limiting examples of suitable structured fluid delivery systems may include nanoparticles, liposomes, microemulsions, micelles, dendrimers and other phospholipid-containing systems. Methods of incorporating agents of the present disclosure into delivery vehicles are known in the art. Although various embodiments are presented below, it will be appreciated that other methods known in the art to incorporate an antigen-binding molecule, as described herein, into a delivery vehicle are contemplated.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. An antigen-binding molecule of the present disclosure can be administered on multiple occasions. Intervals between single dosages can be daily, weekly, monthly or yearly. Intervals can also be irregular as indicated by measuring blood levels of modified polypeptide or antigen in the patient. Alternatively, the antigen-binding molecule can be administered as a sustained release formulation, in which case less frequent administration is required. Dosage and frequency vary depending on the half-life of the polypeptide in the patient.

It may be advantageous to formulate compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutically acceptable carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Dosages and therapeutic regimens of the antigen-binding molecule can be determined by a skilled artisan. In certain embodiments, the antigen-binding molecule is administered by injection (e.g., subcutaneously or intravenously) at a dose of about 0.01 to 40 mg/kg, e.g., 0.01 to 0.1 mg/kg, e.g., about 0.1 to 1 mg/kg, about 1 to 5 mg/kg, about 5 to 25 mg/kg, about 10 to 40 mg/kg. The dosing schedule can vary from e.g., once a week to once every 2, 3, or 4 weeks.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

Disclosed herein is an antigen-binding molecule as defined herein, a chimeric molecule as define herein or a pharmaceutical composition as defined herein for use as a medicament.

Disclosed herein is a method for reducing or inhibiting proliferation and/or viability of a cancer cell, the method comprising contacting the cancer cell with a therapeutically effective amount of an antigen-binding molecule as defined herein, a chimeric molecule as defined herein or a pharmaceutical composition as defined herein.

The terms “cancer” and “cancerous” refer to or describe the physiological condition in mammals that is typically characterized in part by unregulated cell growth. As used herein, the term “cancer” refers to non-metastatic and metastatic cancers, including early stage and late stage cancers. By “non-metastatic” is meant a cancer that remains at the primary site and has not penetrated into the lymphatic or blood vessel system or to tissues other than the primary site. The term “metastatic cancer” refers to cancer that has spread or is capable of spreading from one part of the body to another. Generally, a non-metastatic cancer is any cancer that is a Stage 0, I, or II cancer, and occasionally a Stage III cancer. A metastatic cancer, on the other hand, is usually a stage IV cancer.

The term “cancer” includes but is not limited to, breast cancer, large intestinal cancer, lung cancer, small cell lung cancer, gastric (stomach) cancer, liver cancer, blood cancer, bone cancer, pancreatic cancer, skin cancer, head and/or neck cancer, cutaneous or intraocular melanoma, uterine sarcoma, ovarian cancer, rectal or colorectal cancer, anal cancer, colon cancer, fallopian tube carcinoma, endometrial carcinoma, cervical cancer, vulval cancer, squamous cell carcinoma, vaginal carcinoma, Hodgkin’s disease, non-Hodgkin’s lymphoma, esophageal cancer, small intestine cancer, endocrine cancer, thyroid cancer, parathyroid cancer, adrenal cancer, soft tissue tumor, urethral cancer, penile cancer, prostate cancer, chronic or acute leukemia, lymphocytic lymphoma, bladder cancer, kidney cancer, ureter cancer, renal cell carcinoma, renal pelvic carcinoma, CNS tumor, glioma, astrocytoma, glioblastoma multiforme, primary CNS lymphoma, bone marrow tumor, brain stem nerve gliomas, pituitary adenoma, uveal melanoma (also known as intraocular melanoma), testicular cancer, oral cancer, pharyngeal cancer or a combination thereof.

In one embodiment, the cancer cell is a solid or haematological cancer cell.

The term “haematological cancer’ may refer to one or more of leukemia, lymphoma, Chronic Myeloproliferative Disorders, Langerhans Cell Histiocytosis, Multiple Myeloma/Plasma Cell Neoplasm, Myelodysplasia Syndromes, Myelodysplastic/Myeloproliferative Neoplasms or a combination thereof. In some embodiments, leukemia is any one or more of Acute Lymphoblastic Leukemia (ALL), Acute Myeloid Leukemia (AML), Chronic Lymphocytic Leukemia (CLL), Chronic Myelogenous Leukemia (CML), Hairy Cell Leukemia (HCL) or a combination thereof. In some embodiments, lymphoma is any one or more of AIDS-Related Lymphoma, Cutaneous T-Cell Lymphoma, Hodgkin Lymphoma, Mycosis Fungoides, Non-Hodgkin Lymphoma, Primary Central Nervous System Lymphoma, Sezary Syndrome, T-Cell Lymphoma, Cutaneous, Waldenstrom Macroglobulinemia, B cell lymphoma or a combination thereof.

In one embodiment, the cancer cell is a lymphoma cell. In one embodiment, the lymphoma cell is a B lymphoma cell.

In one embodiment, the subject is suffering from a lymphoma. The subject may be suffering from B cell lymphoma.

The term “solid cancer” may refer to one or more of breast cancer, large intestinal cancer, lung cancer, small cell lung cancer, gastric (stomach) cancer, liver cancer, bone cancer, pancreatic cancer, skin cancer, head and/or neck cancer, cutaneous or intraocular melanoma, uterine sarcoma, ovarian cancer, rectal or colorectal cancer, anal cancer, colon cancer, fallopian tube carcinoma, endometrial carcinoma, cervical cancer, vulval cancer, squamous cell carcinoma, vaginal carcinoma, esophageal cancer, small intestine cancer, endocrine cancer, thyroid cancer, parathyroid cancer, adrenal cancer, soft tissue tumor, urethral cancer, penile cancer, prostate cancer, bladder cancer, kidney cancer, ureter cancer, renal cell carcinoma, renal pelvic carcinoma, CNS tumor, glioma, astrocytoma, glioblastoma multiforme, primary CNS lymphoma, bone marrow tumor, brain stem nerve gliomas, pituitary adenoma, uveal melanoma (also known as intraocular melanoma), testicular cancer, oral cancer, pharyngeal cancer, sarcomas or a combination thereof.

In one embodiment, the cancer is a metastatic cancer. The cancer may be a refractory or a relapsed cancer.

Disclosed herein is a method of reducing or inhibiting proliferation, survival and/or viability of a cancer cell in a subject, the method comprising administering a therapeutically effective amount of an antigen-binding molecule as defined herein, a chimeric molecule as defined herein or a pharmaceutical composition as defined herein to the subject.

Disclosed herein is a method of treating a cancer in a subject, the method comprising administering a therapeutically effective amount of an antigen-binding molecule as defined herein, a chimeric molecule as defined herein or a pharmaceutical composition as defined herein to the subject.

Disclosed herein is a method of treating a disease or condition associated with an undesired expression of MHC Class I DLA-12 antigen in a subject, wherein the method comprises administering a therapeutically effective amount of an antigen-binding molecule as defined herein, a chimeric molecule according as defined herein or a pharmaceutical composition as defined herein to the subject.

The term “treating” as used herein may refer to (1) delaying the appearance of one or more symptoms of the condition; (2) inhibiting the development of the condition or one or more symptoms of the condition; (3) relieving the condition, i.e., causing regression of the condition or at least one or more symptoms of the condition; and/or (4) causing a decrease in the severity of the condition or of one or more symptoms of the condition.

The terms “treating”, “treatment” and the like, are used interchangeably herein to mean relieving, reducing, alleviating, ameliorating or otherwise inhibiting the condition, including one or more symptoms of the condition. The terms “prevent”, “preventing”, “prophylaxis”, “prophylactic”, “preventative” and the like are used interchangeably herein to mean preventing or delaying the onset of the condition, or the risk of developing the condition.

The terms "subject", "patient", "host" or "individual" used interchangeably herein, refer to any subject, particularly a vertebrate subject, and even more particularly a mammalian subject, for whom therapy or prophylaxis is desired. Suitable vertebrate animals that fall within the scope of the invention include, but are not restricted to, any member of the subphylum Chordata including primates (e.g., humans, monkeys and apes, and includes species of monkeys such as from the genus *Macaca* (e.g., cynomolgus monkeys such as *Macaca fascicularis*, and/or rhesus monkeys (*Macaca mulatta*)) and baboon (*Papio ursinus*), as well as marmosets (species from the genus *Callithrix*), squirrel monkeys (species from the genus *Saimiri*) and tamarins (species from the genus *Saguinus*), as well as species of apes such as chimpanzees (*Pan troglodytes*)), rodents (e.g., mice rats, guinea pigs), lagomorphs (e.g., rabbits, hares), bovines (e.g., cattle), ovines (e.g., sheep), caprines (e.g., goats), porcines (e.g., pigs), equines (e.g., horses), canines (e.g., dogs), felines (e.g., cats), avians (e.g., chickens, turkeys, ducks, geese, companion birds such as canaries, budgerigars etc.), marine mammals (e.g., dolphins, whales), reptiles (snakes, frogs, lizards etc.), and fish. In one embodiment, the subject is a canine subject. In another embodiment, the subject is a human subject.

The methods as disclosed herein may comprises the administration of a "therapeutically effective amount" of an agent (e.g. an antigen-binding molecule, a chimeric molecule, a polynucleotide, a construct, a vector, a host cell or a pharmaceutical composition) to a subject. As used herein the term "therapeutically effective amount" includes within its meaning a non-toxic but sufficient amount of an agent or compound to provide the desired therapeutic effect. The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

In one embodiment, there is provided an antigen-binding molecule as defined herein, a chimeric molecule as defined herein or a pharmaceutical composition as defined herein for use in reducing or inhibiting proliferation, survival and/or viability of a cancer cell in a subject.

In one embodiment, there is provided the use of an antigen-binding molecule as defined herein, a chimeric molecule as defined herein or a pharmaceutical composition as defined herein in the manufacture of a medicament for reducing or inhibiting proliferation, survival and/or viability of a cancer cell in a subject.

In one embodiment, there is provided an antigen-binding molecule as defined herein, a chimeric molecule as defined herein or a pharmaceutical composition as defined herein for use in treating a cancer in a subject.

In one embodiment, there is provided the use of an antigen-binding molecule as defined herein, a chimeric molecule as defined herein or a pharmaceutical composition as defined herein in the manufacture of a medicament for treating a cancer in a subject.

In one embodiment, there is provided an antigen-binding molecule as defined herein, a chimeric molecule as defined herein or a pharmaceutical composition as defined herein for use in treating a disease or condition associated with an undesired expression of MHC Class I DLA-12 antigen in a subject.

In one embodiment, there is provided the use of an antigen-binding molecule as defined herein, a chimeric molecule as defined herein or a pharmaceutical composition as defined herein in the manufacture of a medicament for treating a disease or condition associated with an undesired expression of MHC Class I DLA-12 antigen in a subject.

Disclosed herein is a method of detecting the likelihood of the presence of a cancer in a subject, the method comprising determining the level of MHC Class I DLA-12 antigen in a sample obtained from the subject, wherein an increased level of MHC Class I DLA-12 antigen as compared to a reference indicates the likelihood of the presence of a cancer in the subject.

In one embodiment, the sample is a cell, tissue or blood sample.

In one embodiment, the method comprises contacting the sample with an antigen-binding molecule as defined herein or a chimeric molecule as defined herein to determine the level of MHC Class I DLA-12 antigen in the sample.

Throughout this specification and the statements which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Those skilled in the art will appreciate that the invention described herein in susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

Certain embodiments of the invention will now be described with reference to the following examples which are intended for the purpose of illustration only and are not intended to limit the scope of the generality hereinbefore described.

EXAMPLES

Example 1 cLy-c10C5 is a chimeric (canine constant region genes-mouse variable region genes) IgGb mAb developed to target B cell lymphoma. It was generated by immunizing B lymphoma cells, cLy-07 to immunocompetent mice. A total of 1521 hybridoma clones were screened for specific binding to B lymphoma and Mast cancer cells but not to normal dog cells (Table 1). The lead candidate clone 10C5 (mouse IgG1) was selected based on highly efficient cytotoxicity to B lymphoma cells as an ADC and low reactivity to normal cells and tissues.

Figure 2:
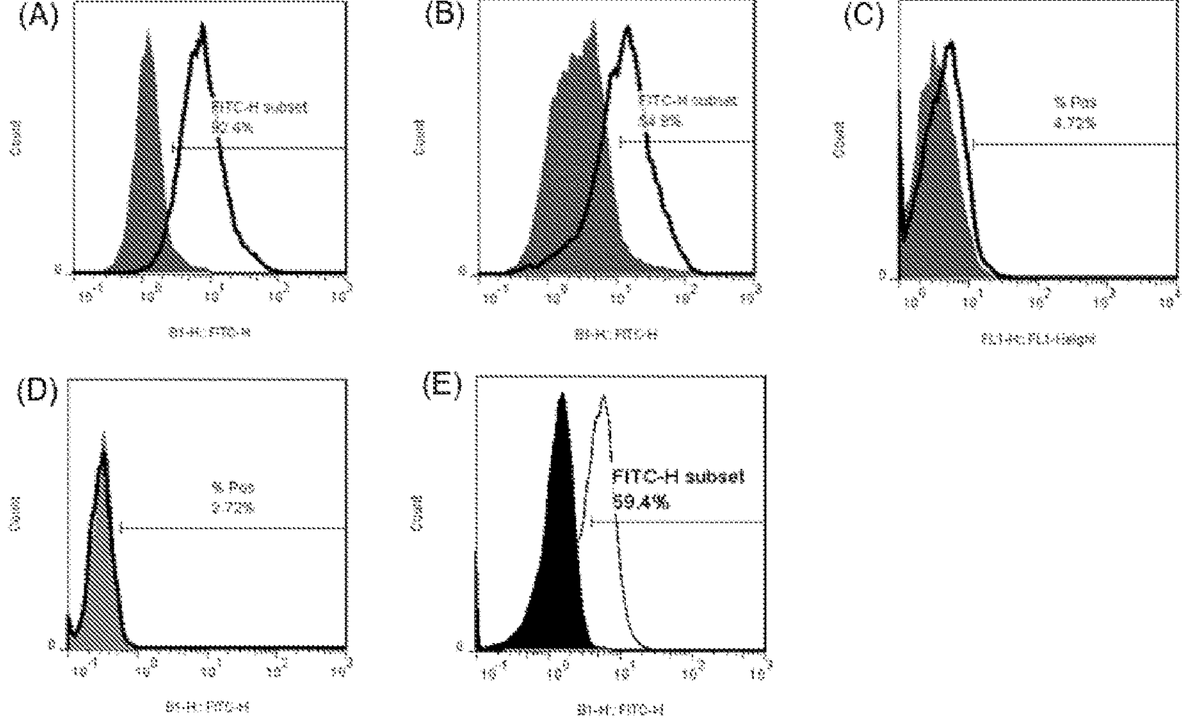
FIG. 2. Flow cytometry data showing cLy-m10C5 binding to various cell lines (A) CLBL-1 (B) cLy09 (C) MDCK (D) cf2TH (E) PBMCs. The cell surface marker that the mAb is binding to is highly expressed in CLBL-1 cells. Shaded peaks for the histogram are negative controls and unshaded peaks are cLy-m10C5 binding.
Figure 3:
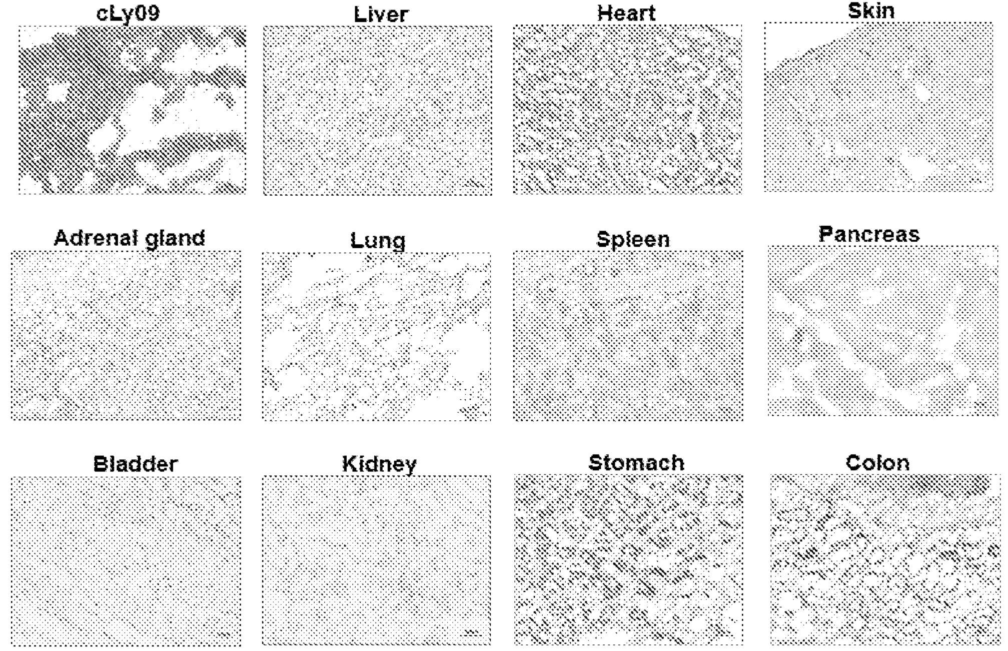
FIG. 3. Immunohistochemistry staining of normal canine tissue specimens with cLy-m10C5. The mAb did not stain most of the normal dog tissues derived from major organs. Positive staining of cLy09 cells used as control. Magnification: 10×
Figure 4:
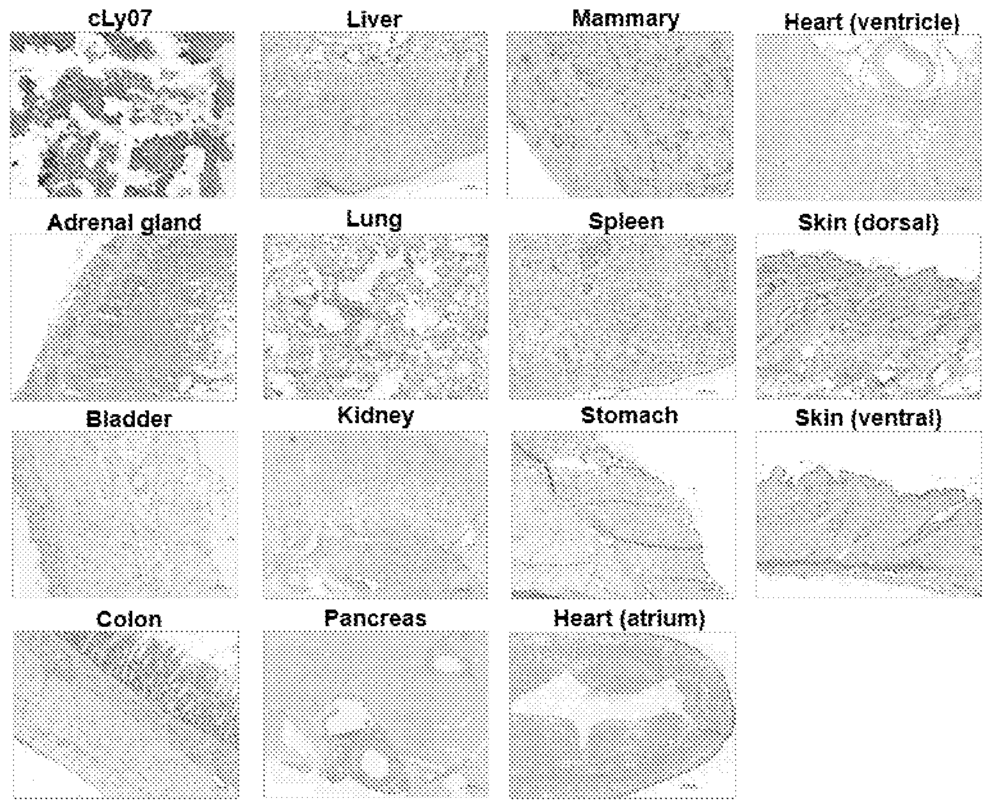
FIG. 4. Immunohistochemistry staining of normal canine tissue specimens with cLy-m10C5, The mAb did not stain most of the normal dog tissues derived from major organs. Positive staining of cLy09 cells used as control. Magnification: 2.5λ.
Figure 5:
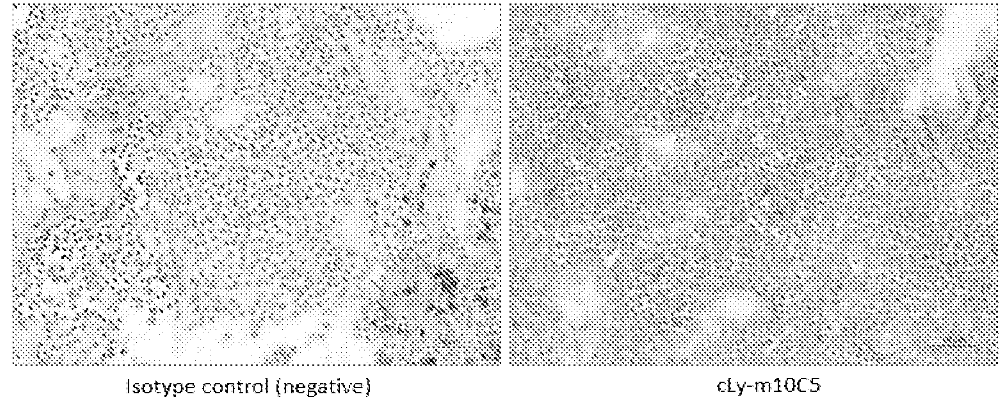
FIG. 5. Immunohistochemistry staining of canine Mast tumour specimens with cLy-m10C5. Staining of Mast cancer tissues is observed.
Figure 6:
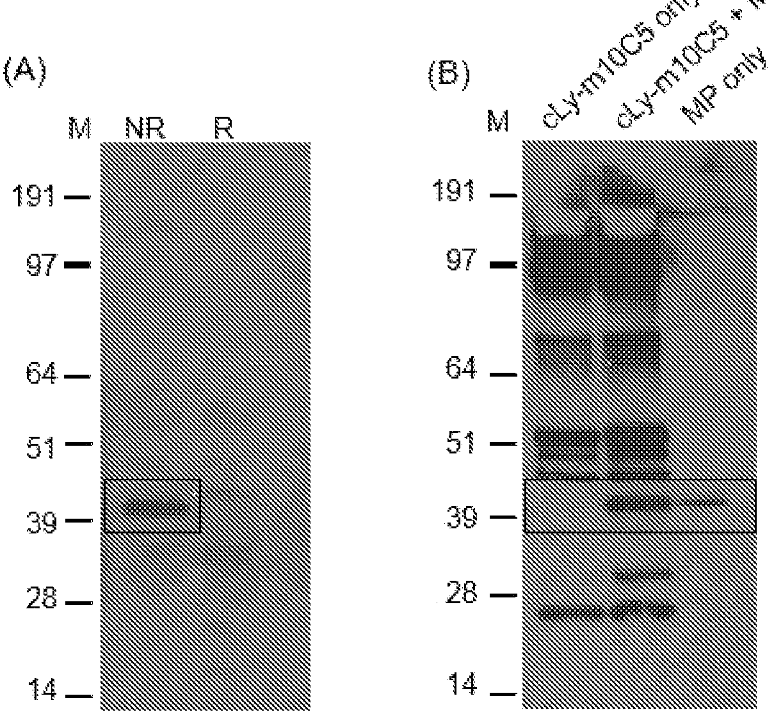
FIG. 6. Identifying the antigen target. cLy-m10C5 binds to a ~42 kDa protein. (A) Western Blot to detect the protein band that cLy-m10C5 binds to and the interaction is lost upon 10% beta-mercaptothanol reducing condition (B) Immunoprecipitation (IP) of antigen target using Protein G capture of mAb cLy-m10C5. A protein band at ~42 kDa was detected after incubating Western blot with cLy-m10C5. The bands were reproduced on a parallel SDS-PAGE gel and excised for mass spectrometry. (MP refers to Membrane Protein).
Figure 7:
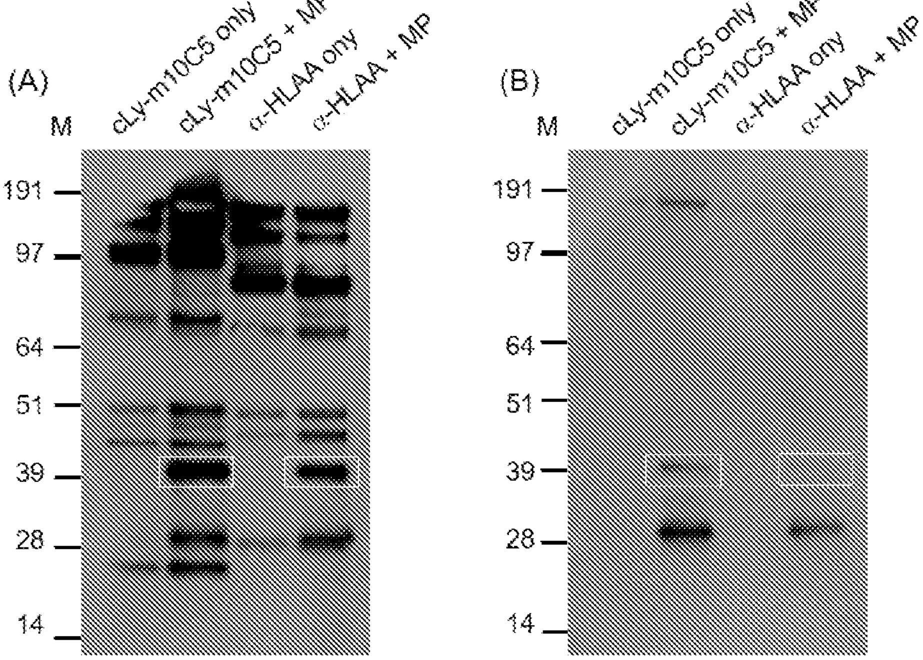
FIG. 7. Validation of antigen target by cross-probing. Commercial antibody from Abcam rabbit α-human HLAA (ab52922) was used for validation. Immunogen for commercial mAb was a synthetic peptide corresponding to human HLAA (aa 50-100). IP samples were run in duplicates on SDS-PAGE and transferred to PVDF blot. Boxed-up band indicate the IP product after blot was incubated with (A) cLy-m10C5 (B) rabbit anti-human HLAA. cLy-m10C5 binds to a MHC class 1-like molecule (DLA-12 in dog, HLAA in human), as suggested by MS data and validated by IP. (MP refers to Membrane Protein).
Figure 8:
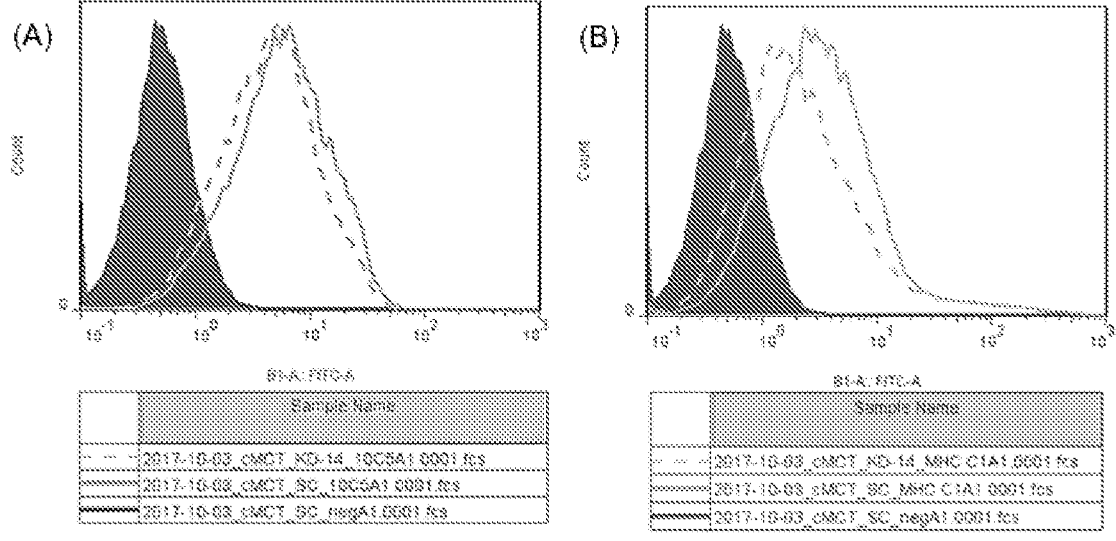
FIG. 8. Flow Cytometry of canine Mast cells transiently transfected with siRNA. Cells treated with siRNA targeting human HLAA (dotted line) were stained for cell surface MHC Class I DLA-12 expression with (A) cLy-m10C5 and (B) anti-MHC Class 1 (AbD Serotec MCA2189). Cells treated with scrambled siRNA (solid line) were used as negative control. Surface expression of MHC Class I (DLA-12) was observed to be reduced after overnight incubation post-nucleofection.
Figure 9:
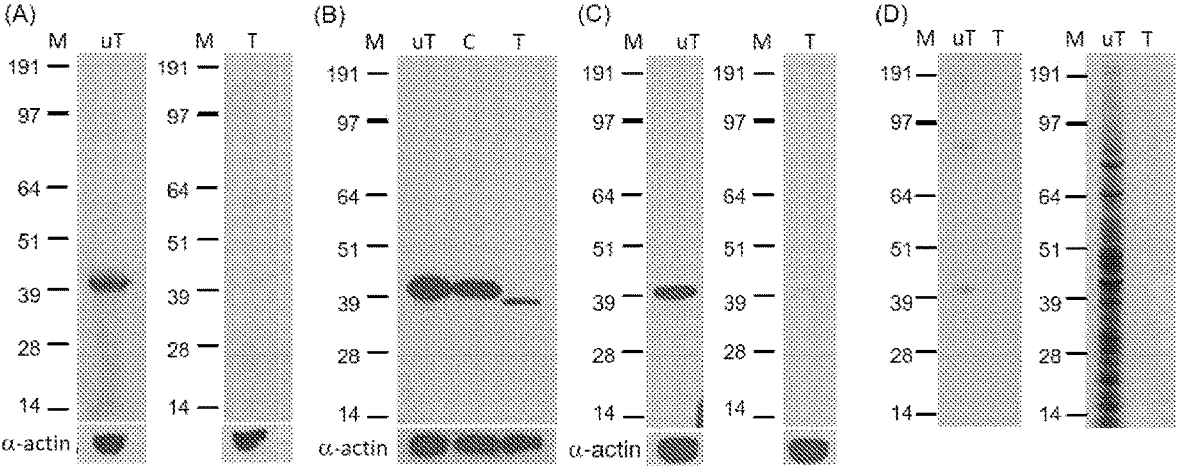
FIG. 9. Binding assays to determine the epitope for cLy-m10C5. (A) Periodate assay showed that cLy-m10C5 binds to a glycan epitope that is sensitive to treatment and loss of binding observed after the removal of glycans. (B) PNGase F treated lysate indicated that cLy-m10C5 binds to a protein after N-glycan removal. (C) O-glycans removal by beta elimination in mild alkaline treatment (50 mM NaOH). Binding of cLy-m10C5 is significantly lost. (D) Loss of mAb binding after Pronase digestion of lysate. Left: cLy-10C5 immunoblot, right: Coomasie stained gel as control. cLy-m10C5 binds to a O-linked glycoprotein epitope of a ~45 kDa protein band uT: untreated samples, C: negative control, T: treated samples.
Figure 10:
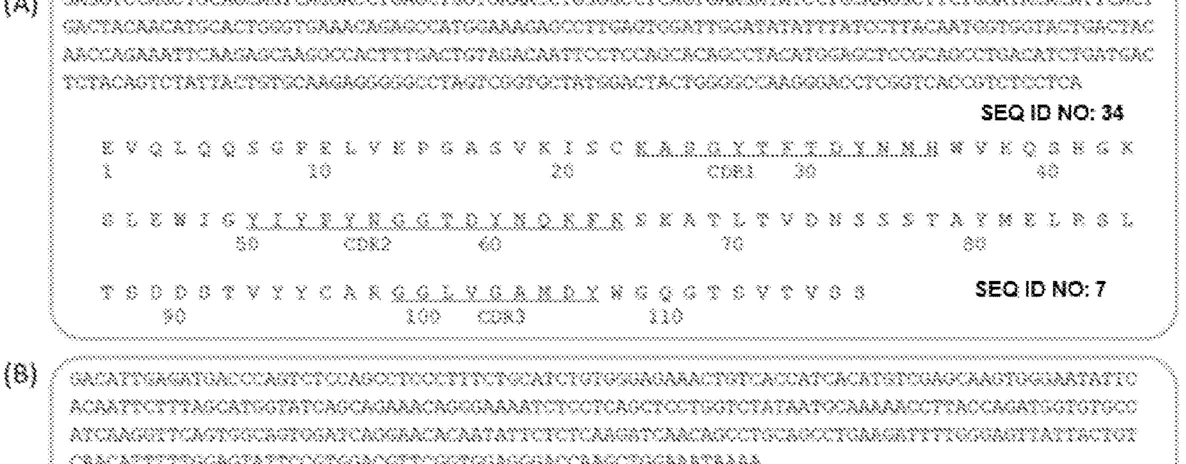
FIG. 10. Sequence of variable region of cLy-c10C5 (A) $V_H$ (B) $V_L$. Underlined sequences depict the CDR regions.

It binds to antigen present on the cell surface of cLy-07, cLy-09, CLBL-1 and Mast cancer cells (cMCT) but not to most normal canine cells and tissues (FIGS. 3-5). However, it binds to normal PBMCs from different dog donor with varying degree (Table 2 and FIG. 2). Several characterization assays were carried out to determine the identity of the antigen. cLy-m10C5 binds to a protein band of molecular weight ~42 kDa (FIG. 6A). IP of antigen using Protein G capture of cLy-m10C5 was done in duplicate and the samples were reproduced on a parallel SDS-PAGE gel and excised for mass spectrometry (FIG. 6B). The identity of antigen was determined to be, MHC Class I DLA-12, protein accession number 046880 (Table 3). A commercial antibody from Abcam, rabbit α-human HLAA was used for validation. The cross-probing IP data validated that cLy-m10C5 binds to an MHC Class I-like molecule (FIGS. 7A and 7B). From the glycan removal assays, the data suggested that cLy-m10C5 binds to an 0-linked glycoprotein epitope and the binding is sensitive to reducing conditions (FIG. 9).

Figure 11:
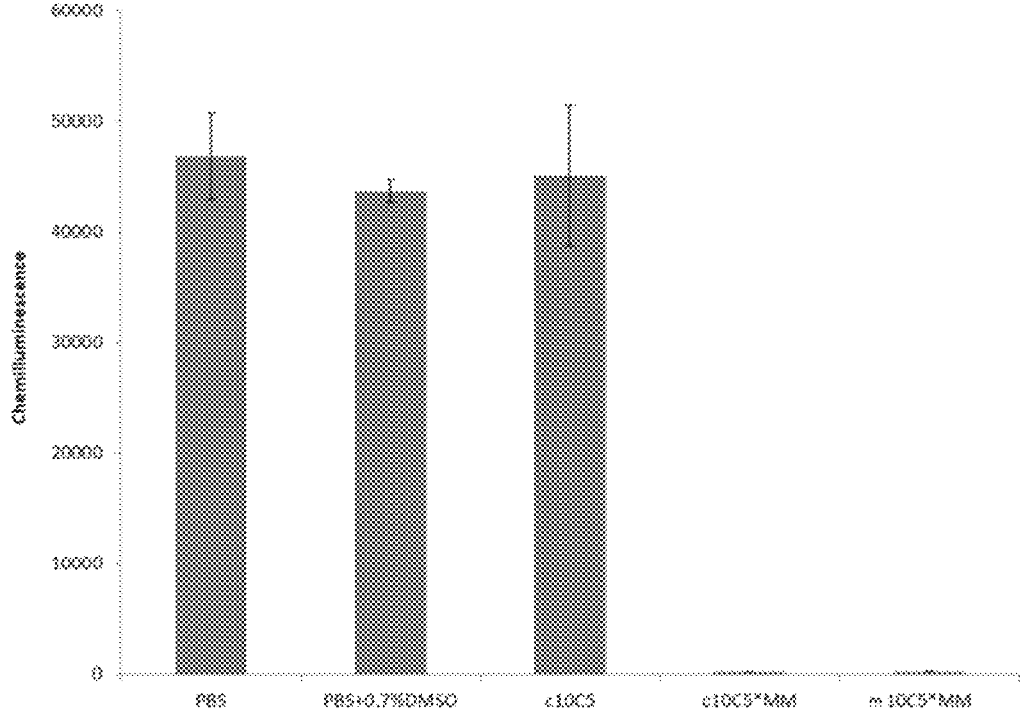
FIG. 11. ADC assay showing the cytotoxic effect of mAb cLy-m10C5 and cLy-c10C5 conjugated to monomethyl auristatin E (MMAE)) (m10C5*MM and c10C5*MM respectively). Comparable cytotoxic effect observed in cLy07 cells for both mouse and canine cLy-10C5 mAbs 72 hrs after spiking in culture. Detection with Cell-Titre-GLO (CTG) kit from Promega and chemilluminesce was recorded with a Tecan Spectrophotometer.
Figure 12A:
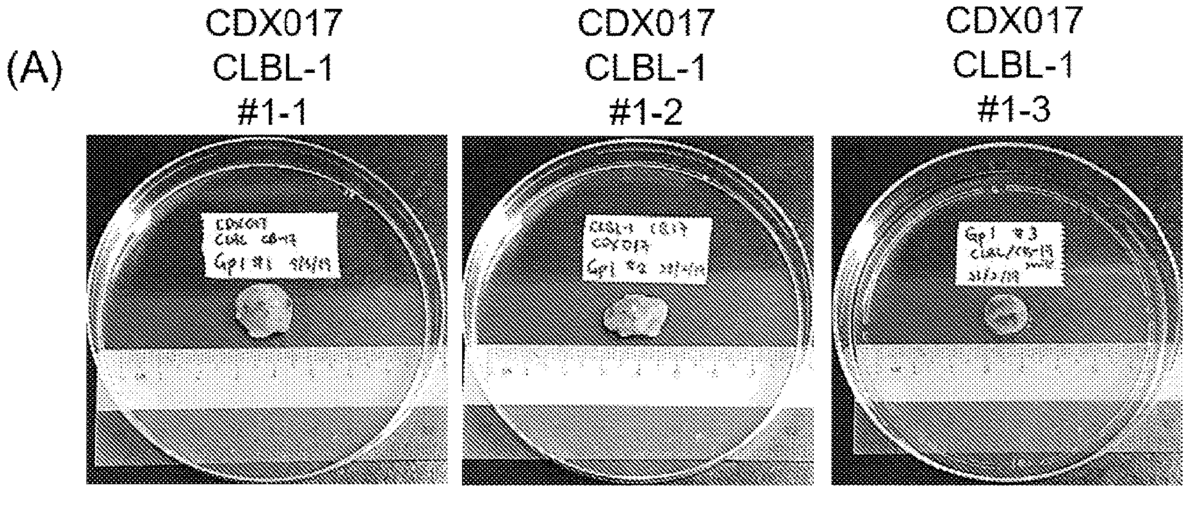
FIG. 12. Characterization of tumours formed in CB-17 SCID mice treated with PBS (control). (A) Tumours formed were well-vascularized (B) Tumours expressed antigens that cLy-m10C5 binds to. Controls for experiment were included; cLy11A12 (negative control) and CD20 (positive control).
Figure 12A:
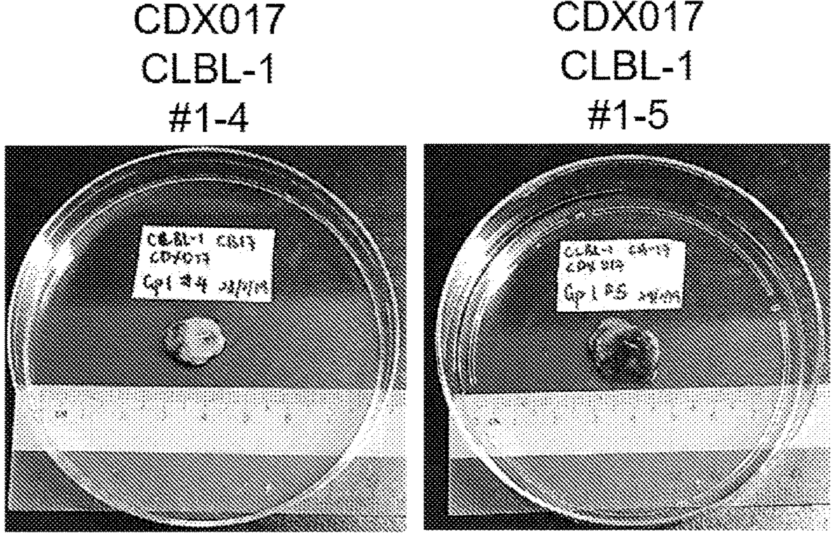
Figure 13:
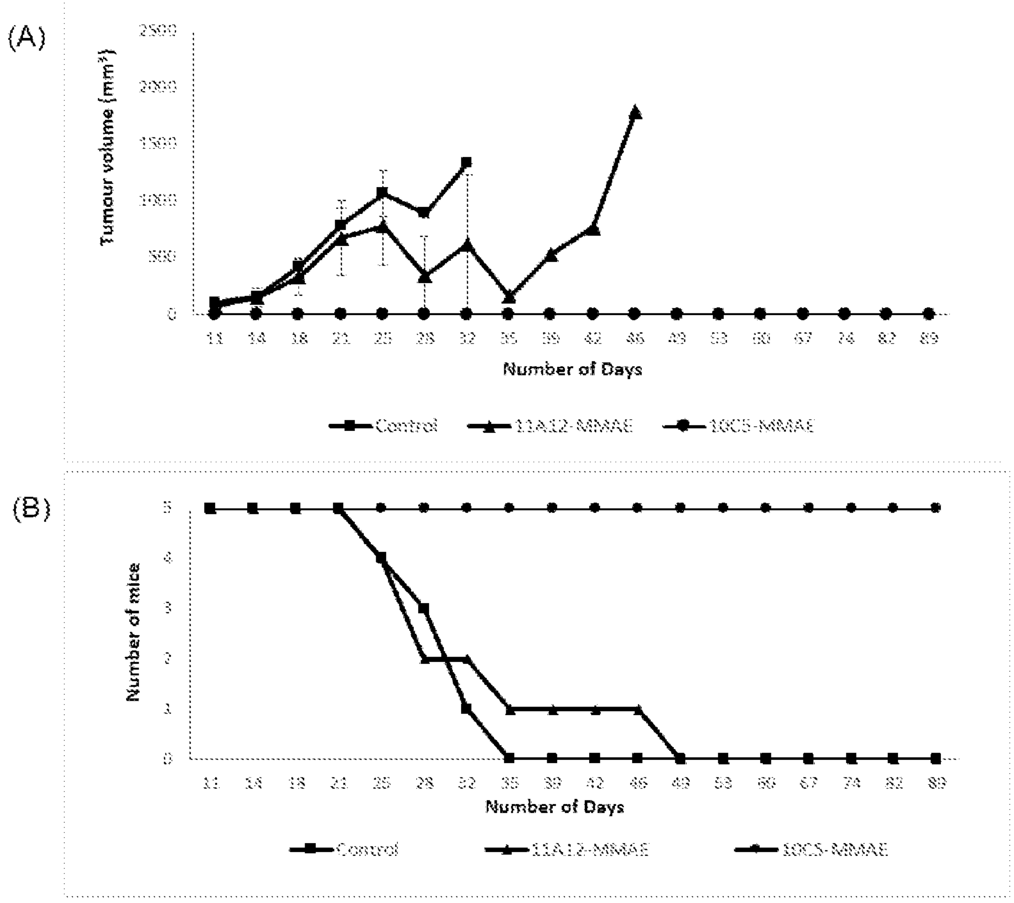
FIG. 13. Treatment of mice inoculated with $2e^6$ CLBL-1 cells. Intraperitoneal doses were given on Day 1, 7 and 14 (Dose 1Q3W). (A) Mice treated with cLy-m10C5-MMAE did not have tumour formation (B) Survival of mice in the different treatment groups. Mice were culled when tumour volume reached 1000 $mm^3$ or if ulceration was observed. cLy-m10C5-MMAE was efficacious to inhibit CLBL-1 cells and prevented B lymphoma tumour growth in mice for more than 90 days. cLy-11A12 was used as an isotype control.

In cell-based assay, cytotoxicity was observed when cLy-c10C5 was conjugated to MMAE (FIG. 11). In vivo animal models were set up to study both efficacy and dose escalation of cLy-10C5-MMAE. Since cLy-m10C5 binds to CLBL-1, it was used as a surrogate cell line for xenograft development and in vivo animal models. For efficacy studies, immunocompromised mice were inoculated with CLBL-1 cells and given treatment with cLy-m10C5-MMAE in a chase model. Groups of mice were given a total of 3 treatments, once every 4 days, via intraperitoneal administration route. Mice treated with cLy-m10C5-MMAE did not produce tumour while control groups given buffer had to be terminated after tumour volume reached 1000 $mm^3$ or when ulceration was observed (FIGS. 12-13).

cLy-m10C5 was converted to a chimeric mAb by replacing the Fc region with a canine IgGb equivalent and the translated heavy and light chain protein sequence have been mapped by DNA sequencing. There was no observed change in the specificity and function between the mouse and chimeric mAb (FIG. 11).

Figure 14A:
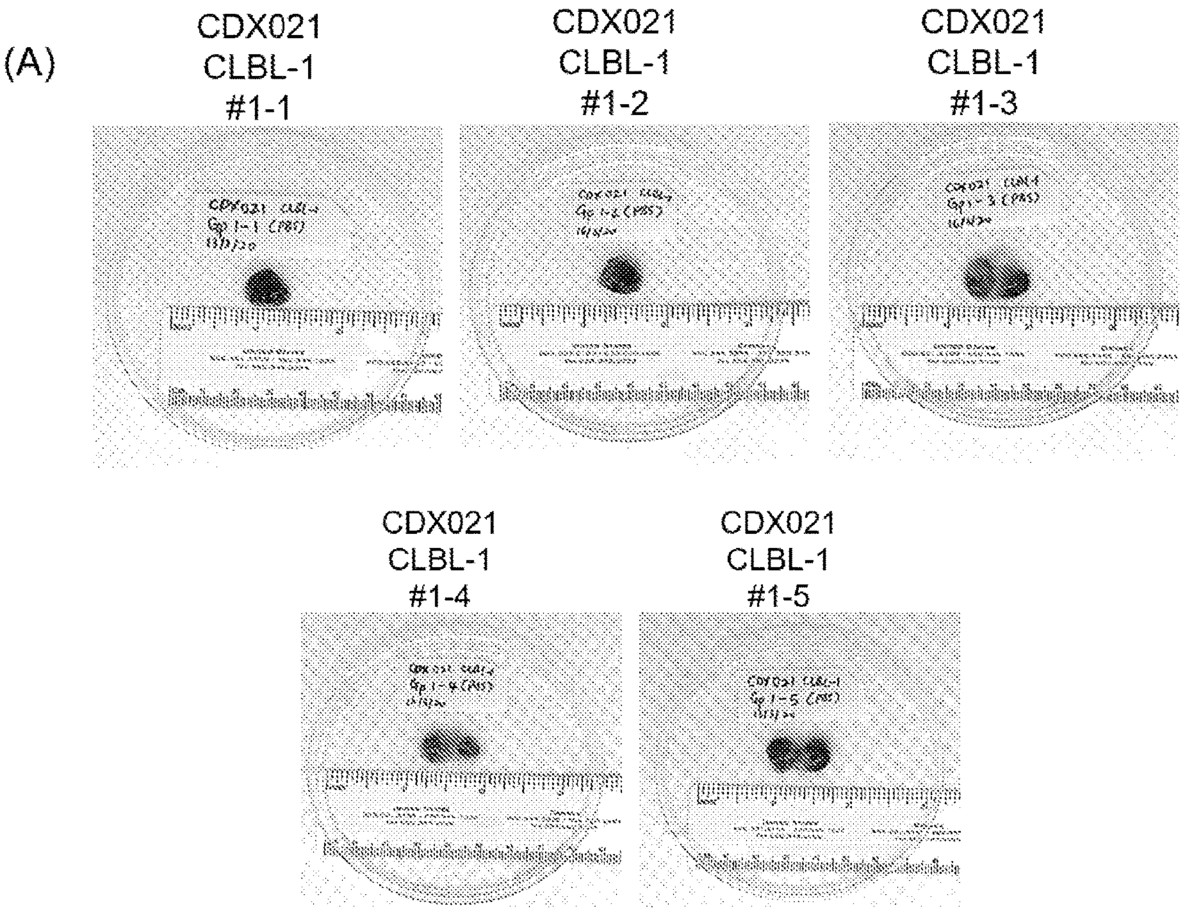
Figure 15:
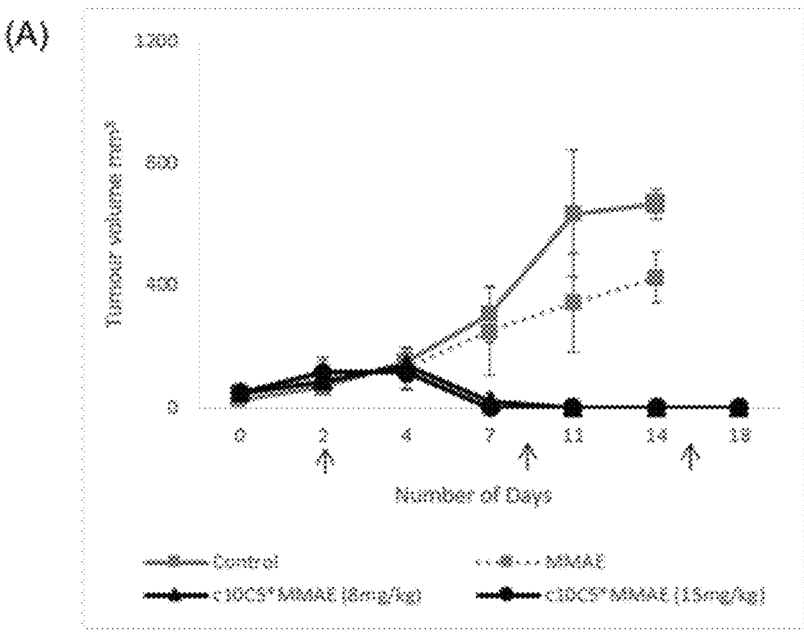
FIG. 15. Dose escalation studies of cLy-c10C5-MMAE on immunodeficient mice. Groups of mice were inoculated subcutaneously with $2e^6$ CLBL-1 cells. Intravenous doses (arrows) were given once a week for 3 weeks to randomized mice when tumours reached 100-150 $mm^3$. (A) Tumour regression observed for mice treated with both doses of cLy-c10C5-MMAE (8 and 15 mg/kg) over more than 30 days (B) Survival of mice in the different treatment groups. The groups of mice were observed for more than 30 days and no relapse was observed.
Figure 15:
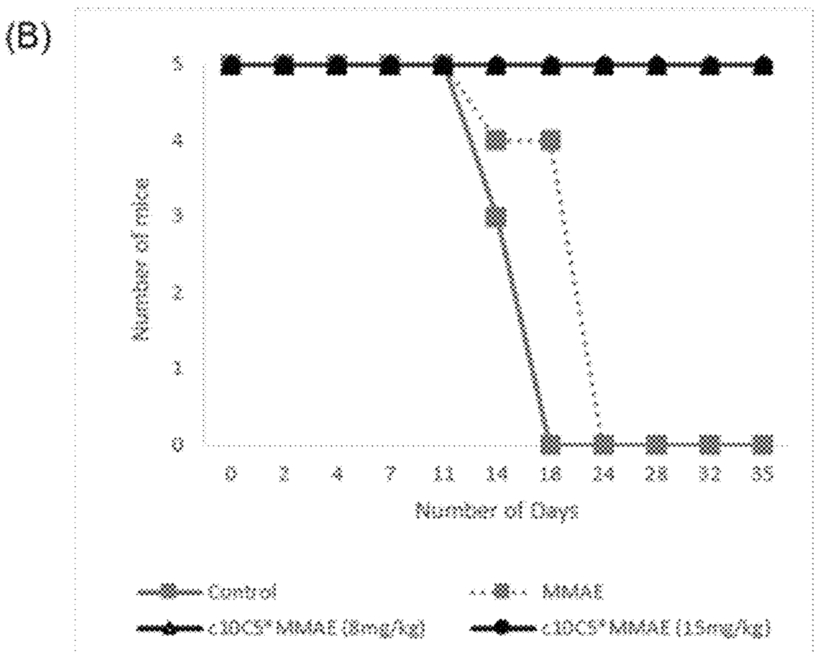
Figure 16:
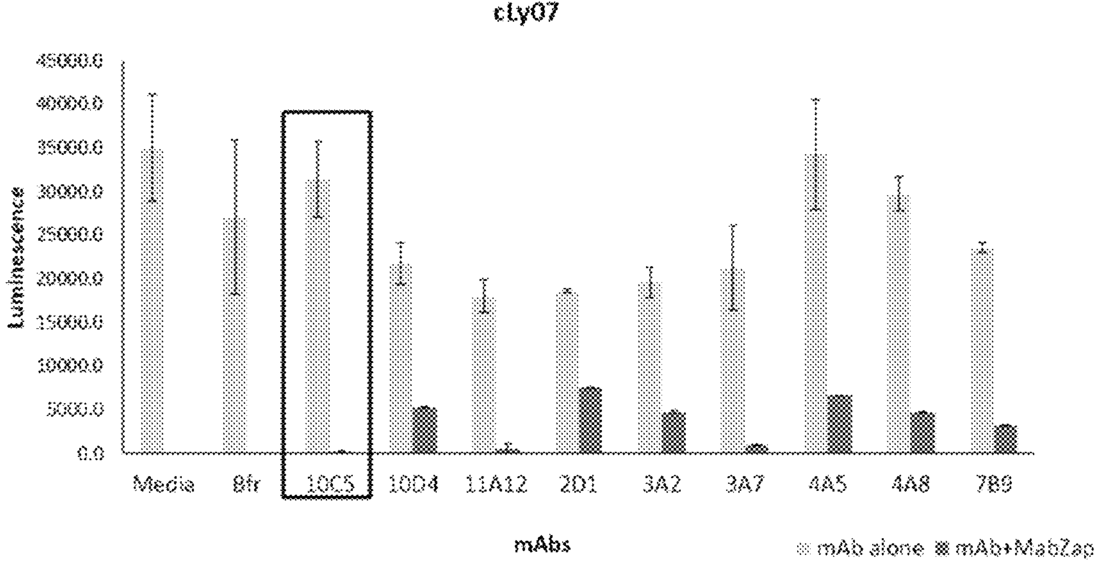
FIG. 16. Cell proliferation assay—Toxin MabZap was used for ADC.

In dose escalation experiments, the mice were inoculated with CLBL-1 cells to allow tumour formation prior to treatment. The tumour-bearing mice were randomized and 2 treatment doses of cLy-c10C5-MMAE were investigated. Tumour regression was observed for mice treated with cLy-c10C5-MMAE (FIGS. 14-15) for more than 30 days. cLy-c10C5-MMAE has potential to be developed as an antibody-drug conjugate (ADC).

TABLE 1

Screening of clones by Flow Cytometry. A total of 1521 clones were obtained and they were selected for their reactivity to other dog cancer cells. The lead candidate 10C5 (boxed) was chosen for further characterization and development due to the high binding affinity to lymphoma cells.

| Tier 1 | | Lymphoma | | Hemangio | Mast | | Tier 2 | | Lymphoma | | Hemangio |
|---|---|---|---|---|---|---|---|---|---|---|---|
| (12) | Isotype | cLy07 | cLy09 | AA88 | cMCT01 | Abby | (19) | Isotype | CLy07 | cLy09 | AA88 |
| 1E11 | IgG | ++ | + | – | +++ | +++ | 1D6 | IgG | ++ | +/– | – |
| 5B9 | IgG | ++ | ++ | – | – | +/– | 2D1 | IgG | ++ | ++ | – |
| 5B11 | IgG | ++ | ++ | – | ++ | +++ | 3A2 | IgG | ++ | ++ | – |
| 6A11 | IgG | ++ | +/– | – | +++ | +++ | 3A7 | IgG | ++ | ++ | – |
| 7C12 | IgG | + | +/– | – | ++ | ++ | 3B5 | IgG | + | ++ | – |
| 7D6 | IgG | ++ | + | – | ++ | ++ | 4A5 | IgG | ++ | ++ | – |
| 9D12 | IgG | ++ | +/– | – | ++ | +++ | 4A8 | IgG | ++ | ++ | – |
| 9E5 | IgG | ++ | + | – | ++ | +++ | 7B9 | IgG | ++ | ++ | – |
| 10C5 | IgG | ++ | ++ | – | ++ | ++ | 8B4 | IgG | ++ | ++ | – |
| 10D4 | IgG | ++ | ++ | – | – | +/– | 8D12 | IgG | ++ | ++ | – |
| 11A12 | IgG | ++ | + | – | +/– | +++ | 8E3 | IgG | ++ | + | – |
| *12B1 | IgM | ++ | ++ | + | – | +/– | 8E12 | IgG | ++ | + | – |
| | | | | | | | 9D3 | IgG | ++ | ++ | – |
| | | | | | | | 10A5 | IgG | ++ | ++ | – |
| | | | | | | | 10C10 | IgG | + | +/– | – |
| | | | | | | | 10C11 | IgG | ++ | + | – |
| | | | | | | | 10E1 | IgG | ++ | ++ | – |
| | | | | | | | 11E8 | IgG | ++ | ++ | – |
| | | | | | | | 11F10 | IgG | ++ | ++ | – |

| Mast | | Tier 3 | | Lymphoma | | Hemangio | Mast | |
|---|---|---|---|---|---|---|---|---|
| cMCT01 | Abby | (4) | Isotype | cLy07 | cLy09 | AA88 | cMCT01 | Abby |
| – | – | 1D5 | IgG | +/– | – | + | – | – |
| – | – | 2D11 | IgG | + | – | – | – | + |
| – | – | 5A10 | IgG | +/– | – | + | – | – |
| – | – | 7D12 | IgG | + | – | +/– | – | – |
| – | – | | | | | | | |
| – | – | | | | | | | |
| – | – | | | | | | | |
| – | – | | | | | | | |
| – | – | | | | | | | |
| – | – | | | | | | | |
| – | – | | | | | | | |
| – | – | | | | | | | |
| – | – | | | | | | | |
| – | – | | | | | | | |
| – | – | | | | | | | |

TABLE 1-continued

Screening of clones by Flow Cytometry. A total of 1521 clones were obtained and they were selected for their reactivity to other dog cancer cells. The lead candidate 10C5 (boxed) was chosen for further characterization and development due to the high binding affinity to lymphoma cells.

| | | |
|---|---|---|
| | – | – |
| | – | – |
| | – | – |
| | – | – |

<10% –
10-20% +/–
21-30% +
31-50% ++
51-100% +++

TABLE 2

Binding profile of cLy-m10C5 to (A) normal canine cells (B) canine cancer cells. The cell surface protein that cLy-m10C5 binds to is also expressed in canine mast cancer cells and to varying degree in normal PBMCs.

(A)

| PBMC | | | Kidney | Thymus |
|---|---|---|---|---|
| AVA_01 | AVA_02 | AVA_04 | MDCK | Cf2Th |
| – | – | ++ | – | – |

(B)

| Lymphoma | Mast | | Hemangio-sarcoma | Melanoma | Mammary | |
|---|---|---|---|---|---|---|
| cLyC09 | cMCT01 | Abby | AA88 | cMel | Silky | AT1 |
| ++ | ++ | ++ | – | – | – | – |

<10% –
10-20% +/–
21-30% +
31-50% ++
51-100% +++

TABLE 3

Mass spectrometry (MS) identified the protein that cLy-m10C5 targeted is MHC Class I DLA-12.

| Accession | Description | Score | MW [kDa] | Coverage | # Pro-teins | # Unique Peptides | # Peptides |
|---|---|---|---|---|---|---|---|
| F1PEZ8 | Uncharacterized protein OS = *Canis lupus familiaris* GN = DLA-12 PE = 3 SV = 2-[F1PEZ8_CANLF] | 66.84 | 40.1 | 29.44 | 1 | 1 | 8 |
| O46880 | MHC class I DLA-12 OS = *Canis lupus familiaris* PE = 3 SV = 1-[O46880_CANLF] | 66.79 | 39.8 | 33.52 | 1 | 2 | 9 |

| | A2 | Sequence | q- | # PSMs | # | # | Protein Group |
|---|---|---|---|---|---|---|---|
| | High | DGEDQT QDTEVV DTRPAG DGTFQK (SEQ ID NO: 11) | 0 | 2 | 2 | 2 | F1PEZ8; O46880 |

TABLE 3-continued

Mass spectrometry (MS) identified the protein that cLy-m10C5 targeted is MHC Class I DLA-12.

| | | | | | | | |
|---|---|---|---|---|---|---|---|
| | High | APWVEQ EGPEYW DPQTR (SEQ ID NO: 12) | 0 | 2 | 1 | 1 | O46880 |
| | High | HPVSDH EVTLR (SEQ ID NO: 13) | 0 | 5 | 2 | 2 | F1PEZ8; O46880 |
| | High | DDSAQG SDVSLT APR (SEQ ID NO: 14) | 0 | 2 | 2 | 2 | F1PEZ8; O46880 |
| | High | NYLETT CVEWLR (SEQ ID NO: 15) | 0 | 1 | 2 | 2 | F1PEZ8; O46880 |
| | High | SWTAAD AAAQIT R (SEQ ID NO: 16) | 0 | 1 | 1 | 1 | O46880 |
| | High | GPGYSH AAR (SEQ ID NO: 17) | 0 | 7 | 2 | 2 | F1PEZ8; O46880 |
| | High | FDSDAA TGR (SEQ ID NO: 18) | 0 | 3 | 2 | 2 | F1PEZ8; O46880 |
| | High | EAAGDA GHLR (SEQ ID NO: 19) | 0 | 1 | 2 | 2 | F1PEZ8; O46880 |

| Accession | Description | Score | MW [kDa] | Coverage | # Pro-teins | # Unique Peptides | # Peptides |
|---|---|---|---|---|---|---|---|
| O46880 | MHC class I DLA-12 OS = *Canis lupus familiaris* PE = 3 SV = 1- [O46880_CANLF] | 85.26 | 39.8 | 50.28 | 1 | 4 | 14 |

| | A2 | Sequence | q-Value | # PSMs | # Proteins | # Protein Groups | Protein Group Accessions |
|---|---|---|---|---|---|---|---|
| | High | DGEDQT QDTEVV DTRPAG DGTFQK (SEQ ID NO: 20) | 0 | 4 | 2 | 2 | O46882; O46880 |
| | High | HPVSDH EVTLR (SEQ ID NO: 21) | 0 | 5 | 1 | 1 | O46880 |
| | High | APWVEQ EGPEYW DPQTR (SEQ ID NO: 22) | 0 | 3 | 1 | 1 | O46880 |

TABLE 3-continued

Mass spectrometry (MS) identified the protein that cLy-m10C5 targeted is MHC Class I DLA-12.

| | | | | | | |
|---|---|---|---|---|---|---|
| High | DDSAQG SDVSLT APR (SEQ ID NO: 23) | 0 | 2 | 2 | 2 | O46882; O46880 |
| High | WAAVVV PSGQEQ R (SEQ ID NO: 24) | 0 | 2 | 2 | 2 | O46882; O46880 |
| High | GYSQDA YDGADY IALNED LR (SEQ ID NO: 25) | 0 | 1 | 2 | 2 | O46882; O46880 |
| High | NYLETT CVEWLR (SEQ ID NO: 26) | 0 | 1 | 2 | 2 | O46882; O46880 |
| High | SWTAAD AAAQIT R (SEQ ID NO: 27) | 0 | 1 | 1 | 1 | O46880 |
| High | GPGYSH AAR (SEQ ID NO: 28) | 0 | 7 | 2 | 2 | O46882; O46880 |
| High | FDSDAA TGR (SEQ ID NO: 29) | 0 | 3 | 2 | 2 | O46882; O46880 |
| High | FIAVGY VDDTQF VR (SEQ ID NO: 30) | 0 | 1 | 2 | 2 | O46882; O46880 |
| High | EAAGDA GHLR (SEQ ID NO: 31) | 0 | 1 | 1 | 1 | O46880 |
| High | VDLDTL R (SEQ ID NO: 32) | 0 | 1 | 2 | 2 | O46882; O46880 |
| High | YLEMGK (SEQ ID NO: 33) | 0 | 1 | 2 | 2 | O46882; O46880 |

TABLE 4

| In vivo tumour-chase animal model. Groups of CB-17 SCIDs mice were inoculated subcutaneously with $2e^6$ CLBL-1 cells. Each group of 5 mice were given a total of 3 doses, 1 dose per week (1Q3W) via intraperitoneal route. Mice were culled when tumour volume exceeds 1000 $mm^3$ or ulceration occurs. | |
|---|---|
| Group | Description |
| 1 | PBS buffer (control) |
| 2 | 11A12*MMAE (isotype control) |
| 3 | 10C5*MMAE |

TABLE 5

| In vivo animal model using CB-17 SCIDs mice with established tumours (~100 $mm^3$). Groups of mice were inoculated subcutaneously with $2e^6$ CLBL-1 cells. Each group of 5 mice were given a total of 3 doses, 1 dose per week (1Q3W) via intravenous route. Mice were culled when tumour volume exceeded 1000 $mm^3$ or when ulceration occurred. | |
|---|---|
| Group | Description |
| 1 | PBS buffer |
| 2 | MMAE |
| 3 | c10C5*MMAE (8 mg/kg) |
| 4 | c10C5*MMAE (15 mg/kg) |

The invention claimed is:

1. An antigen-binding molecule that specifically binds to MHC Class I DLA-12 antigen, wherein the antigen-binding molecule comprises:

a) a heavy chain variable (VH) region comprising the VHCDR1 amino acid sequence K A S G Y T F T D Y N M H (SEQ ID NO: 1), the VHCDR2 amino acid sequence Y I Y P Y N G G T D Y N Q K F K (SEQ ID NO: 2) and the VHCDR3 amino acid sequence G G L V G A M D Y (SEQ ID NO: 3); and b) a light chain variable (VL) region comprising the VLCDR1 amino acid sequence R A S G N I H N S L A (SEQ ID NO: 4), the VLCDR2 amino acid sequence N A K T L P D (SEQ ID NO: 5) and the VLCDR3 amino acid sequence Q H F W S I P W T (SEQ ID NO: 6).

2. The antigen-binding molecule of claim 1, wherein the MHC Class I DLA-12 antigen is a canine MHC Class I DLA-12 antigen.

3. The antigen-binding molecule of claim 1, wherein the antigen-binding molecule comprises:

a) a VH region comprising an amino acid sequence having at least 70% sequence identity to:

```
                                     (SEQ ID NO: 7)
E V Q L Q Q S G P E L V K P G A S V K I S C K A S

G Y T F T D Y N M H W V K Q S H G K S L E W I G Y

I Y P Y N G G T D Y N Q K F K S K A T L T V D N S

S S T A Y M E L R S L T S D D S T V Y Y C A R G G

L V G A M D Y W G Q G T S V T V S S;
```

and b) a VL region comprising an amino acid sequence having at least 70% sequence identity to:

```
                                     (SEQ ID NO: 8)
D I Q M T Q S P A S L S A S V G E T V T I T C R A

S G N I H N S L A W Y Q Q K Q G K S P Q L L V Y N

A K T L P D G V P S R F S G S G S G T Q Y S L K I

N S L Q P E D F G S Y Y C Q H F W S I P W T F G G

G T K L E I K.
```

4. The antigen-binding molecule of claim 1, wherein the antigen-binding fragment is an antibody or antigen-binding fragment thereof.

5. The antigen-binding molecule of claim 4, wherein the antibody or antigen-binding fragment thereof is caninized or chimerized.

6. The antigen-binding molecule of claim 4, wherein the antibody or antigen-binding fragment thereof is a full-length antibody, a Fab fragment, a scFab, a Fab', a single chain variable fragment (scFv) or a one-armed antibody.

7. The antigen-binding molecule of claim 6, wherein the antibody or antigen-binding fragment thereof is a full-length antibody and comprises a canine constant region.

8. A chimeric molecule comprising an antigen-binding molecule according to claim 1 and a heterologous moiety.

9. The chimeric molecule of claim 8, wherein the heterologous moiety is a detectable moiety, a half-life extending moiety or a therapeutic moiety.

10. The chimeric molecule of claim 9, wherein the therapeutic moiety is a toxin.

11. The chimeric molecule of claim 10, wherein the toxin is auristatin, saporin, Mertansine (DM1).

12. The chimeric molecule of claim 11, wherein the auristatin is Monomethyl auristatin E (MMAE).

13. A pharmaceutical composition comprising an antigen-binding molecule according to claim 1.

14. A method of treating cancer in a subject, wherein the method comprises administering a therapeutically effective amount of an antigen-binding molecule that specifically binds to MHC Class I DLA-12 to the subject, and wherein the antigen-binding molecule comprises:

a) a heavy chain variable (VH) region comprising the VHCDR1 amino acid sequence K A S G Y T F T D Y N M H (SEQ ID NO: 1), the VHCDR2 amino acid sequence Y I Y P Y N G G T D Y N Q K F K (SEQ ID NO: 2) and the VHCDR3 amino acid sequence G G L V G A M D Y (SEQ ID NO: 3); and b) a light chain variable (VL) region comprising the VLCDR1 amino acid sequence R A S G N I H N S L A (SEQ ID NO: 4), the VLCDR2 amino acid sequence N A K T L P D (SEQ ID NO: 5) and the VLCDR3 amino acid sequence Q H F W S I P W T (SEQ ID NO: 6).

* * * * *

SEQUENCE LISTING

```
<160> NUMBER OF SEQ ID NOS: 35

<210> SEQ ID NO 1
<211> LENGTH: 13
<212> TYPE: PRT
<213> ORGANISM: Artificial Sequence
<220> FEATURE:
<223> OTHER INFORMATION: VH CDR1

<400> SEQUENCE: 1

Lys Ala Ser Gly Tyr Thr Phe Thr Asp Tyr Asn Met His
1               5                   10


<210> SEQ ID NO 2
<211> LENGTH: 16
<212> TYPE: PRT
<213> ORGANISM: Artificial Sequence
<220> FEATURE:
<223> OTHER INFORMATION: VH CDR2

<400> SEQUENCE: 2

Tyr Ile Tyr Pro Tyr Asn Gly Gly Thr Asp Tyr Asn Gln Lys Phe Lys
1               5                   10                  15


<210> SEQ ID NO 3
<211> LENGTH: 9
<212> TYPE: PRT
<213> ORGANISM: Artificial Sequence
<220> FEATURE:
<223> OTHER INFORMATION: VH CDR3

<400> SEQUENCE: 3

Gly Gly Leu Val Gly Ala Met Asp Tyr
1               5


<210> SEQ ID NO 4
<211> LENGTH: 11
<212> TYPE: PRT
<213> ORGANISM: Artificial Sequence
<220> FEATURE:
<223> OTHER INFORMATION: VL CDR1

<400> SEQUENCE: 4

Arg Ala Ser Gly Asn Ile His Asn Ser Leu Ala
1               5                   10


<210> SEQ ID NO 5
<211> LENGTH: 7
<212> TYPE: PRT
<213> ORGANISM: Artificial Sequence
<220> FEATURE:
```

<223> OTHER INFORMATION: VL CDR2

<400> SEQUENCE: 5

Asn Ala Lys Thr Leu Pro Asp
1 5

<210> SEQ ID NO 6
<211> LENGTH: 9
<212> TYPE: PRT
<213> ORGANISM: Artificial Sequence
<220> FEATURE:
<223> OTHER INFORMATION: VL CDR3

<400> SEQUENCE: 6

Gln His Phe Trp Ser Ile Pro Trp Thr
1 5

<210> SEQ ID NO 7
<211> LENGTH: 118
<212> TYPE: PRT
<213> ORGANISM: Artificial Sequence
<220> FEATURE:
<223> OTHER INFORMATION: VH

<400> SEQUENCE: 7

Glu Val Gln Leu Gln Gln Ser Gly Pro Glu Leu Val Lys Pro Gly Ala
1 5 10 15

Ser Val Lys Ile Ser Cys Lys Ala Ser Gly Tyr Thr Phe Thr Asp Tyr
20 25 30

Asn Met His Trp Val Lys Gln Ser His Gly Lys Ser Leu Glu Trp Ile
35 40 45

Gly Tyr Ile Tyr Pro Tyr Asn Gly Gly Thr Asp Tyr Asn Gln Lys Phe
50 55 60

Lys Ser Lys Ala Thr Leu Thr Val Asp Asn Ser Ser Ser Thr Ala Tyr
65 70 75 80

Met Glu Leu Arg Ser Leu Thr Ser Asp Asp Ser Thr Val Tyr Tyr Cys
85 90 95

Ala Arg Gly Gly Leu Val Gly Ala Met Asp Tyr Trp Gly Gln Gly Thr
100 105 110

Ser Val Thr Val Ser Ser
115

<210> SEQ ID NO 8
<211> LENGTH: 107
<212> TYPE: PRT
<213> ORGANISM: Artificial Sequence
<220> FEATURE:
<223> OTHER INFORMATION: VL

<400> SEQUENCE: 8

Asp Ile Gln Met Thr Gln Ser Pro Ala Ser Leu Ser Ala Ser Val Gly
1 5 10 15

Glu Thr Val Thr Ile Thr Cys Arg Ala Ser Gly Asn Ile His Asn Ser
20 25 30

Leu Ala Trp Tyr Gln Gln Lys Gln Gly Lys Ser Pro Gln Leu Leu Val
35 40 45

Tyr Asn Ala Lys Thr Leu Pro Asp Gly Val Pro Ser Arg Phe Ser Gly
50 55 60

Ser Gly Ser Gly Thr Gln Tyr Ser Leu Lys Ile Asn Ser Leu Gln Pro
65 70 75 80

-continued

```
Glu Asp Phe Gly Ser Tyr Tyr Cys Gln His Phe Trp Ser Ile Pro Trp
                85                  90                  95

Thr Phe Gly Gly Gly Thr Lys Leu Glu Ile Lys
            100                 105


<210> SEQ ID NO 9
<211> LENGTH: 333
<212> TYPE: PRT
<213> ORGANISM: Artificial Sequence
<220> FEATURE:
<223> OTHER INFORMATION: Heavy chain constant region

<400> SEQUENCE: 9

Thr Thr Ala Pro Ser Val Phe Pro Leu Ala Pro Ser Cys Gly Ser Thr
1               5                   10                  15

Ser Gly Ser Thr Val Ala Leu Ala Cys Leu Val Ser Gly Tyr Phe Pro
            20                  25                  30

Glu Pro Val Thr Val Ser Trp Asn Ser Gly Ser Leu Thr Ser Gly Val
        35                  40                  45

His Thr Phe Pro Ser Val Leu Gln Ser Ser Gly Leu Tyr Ser Leu Ser
    50                  55                  60

Ser Met Val Thr Val Pro Ser Ser Arg Trp Pro Ser Glu Thr Phe Thr
65                  70                  75                  80

Cys Asn Val Ala His Pro Ala Ser Lys Thr Lys Val Asp Lys Pro Val
                85                  90                  95

Pro Lys Arg Glu Asn Gly Arg Val Pro Arg Pro Pro Asp Cys Pro Lys
            100                 105                 110

Cys Pro Ala Pro Glu Met Leu Gly Gly Pro Ser Val Phe Ile Phe Pro
        115                 120                 125

Pro Lys Pro Lys Asp Thr Leu Leu Ile Ala Arg Thr Pro Glu Val Thr
    130                 135                 140

Cys Val Val Val Asp Leu Asp Pro Glu Asp Pro Glu Val Gln Ile Ser
145                 150                 155                 160

Trp Phe Val Asp Gly Lys Gln Met Gln Thr Ala Lys Thr Gln Pro Arg
                165                 170                 175

Glu Glu Gln Phe Asn Gly Thr Tyr Arg Val Val Ser Val Leu Pro Ile
            180                 185                 190

Gly His Gln Asp Trp Leu Lys Gly Lys Gln Phe Thr Cys Lys Val Asn
        195                 200                 205

Asn Lys Ala Leu Pro Ser Pro Ile Glu Arg Thr Ile Ser Lys Ala Arg
    210                 215                 220

Gly Gln Ala His Gln Pro Ser Val Tyr Val Leu Pro Pro Ser Arg Glu
225                 230                 235                 240

Glu Leu Ser Lys Asn Thr Val Ser Leu Thr Cys Leu Ile Lys Asp Phe
                245                 250                 255

Phe Pro Pro Asp Ile Asp Val Glu Trp Gln Ser Asn Gly Gln Gln Glu
            260                 265                 270

Pro Glu Ser Lys Tyr Arg Thr Thr Pro Pro Gln Leu Asp Glu Asp Gly
        275                 280                 285

Ser Tyr Phe Leu Tyr Ser Lys Leu Ser Val Asp Lys Ser Arg Trp Gln
    290                 295                 300

Arg Gly Asp Thr Phe Ile Cys Ala Val Met His Glu Ala Leu His Asn
305                 310                 315                 320

His Tyr Thr Gln Glu Ser Leu Ser His Ser Pro Gly Lys
                325                 330
```

<210> SEQ ID NO 10
<211> LENGTH: 108
<212> TYPE: PRT
<213> ORGANISM: Artificial Sequence
<220> FEATURE:
<223> OTHER INFORMATION: light chain constant region

<400> SEQUENCE: 10

```
Asp Ala Gln Pro Ala Val Tyr Leu Phe Gln Pro Ser Pro Asp Gln Leu
1               5                   10                  15

His Thr Gly Ser Ala Ser Val Val Cys Leu Leu Asn Ser Phe Tyr Pro
            20                  25                  30

Lys Asp Ile Asn Val Lys Trp Lys Val Asp Gly Val Ile Gln Asp Thr
        35                  40                  45

Gly Ile Gln Glu Ser Val Thr Glu Gln Asp Lys Asp Ser Thr Tyr Ser
    50                  55                  60

Leu Ser Ser Thr Leu Thr Met Ser Ser Thr Glu Tyr Leu Ser His Glu
65                  70                  75                  80

Leu Tyr Ser Cys Glu Ile Thr His Lys Ser Leu Pro Ser Thr Leu Ile
                85                  90                  95

Lys Ser Phe Gln Arg Ser Glu Cys Gln Arg Val Asp
            100                 105
```

<210> SEQ ID NO 11
<211> LENGTH: 24
<212> TYPE: PRT
<213> ORGANISM: Artificial Sequence
<220> FEATURE:
<223> OTHER INFORMATION: MHC class I DLA-12 sequence

<400> SEQUENCE: 11

```
Asp Gly Glu Asp Gln Thr Gln Asp Thr Glu Val Val Asp Thr Arg Pro
1               5                   10                  15

Ala Gly Asp Gly Thr Phe Gln Lys
            20
```

<210> SEQ ID NO 12
<211> LENGTH: 17
<212> TYPE: PRT
<213> ORGANISM: Artificial Sequence
<220> FEATURE:
<223> OTHER INFORMATION: MHC class I DLA-12 sequence

<400> SEQUENCE: 12

```
Ala Pro Trp Val Glu Gln Glu Gly Pro Glu Tyr Trp Asp Pro Gln Thr
1               5                   10                  15

Arg
```

<210> SEQ ID NO 13
<211> LENGTH: 11
<212> TYPE: PRT
<213> ORGANISM: Artificial Sequence
<220> FEATURE:
<223> OTHER INFORMATION: MHC class I DLA-12 sequence

<400> SEQUENCE: 13

```
His Pro Val Ser Asp His Glu Val Thr Leu Arg
1               5                   10
```

<210> SEQ ID NO 14
<211> LENGTH: 15
<212> TYPE: PRT

<213> ORGANISM: Artificial Sequence
<220> FEATURE:
<223> OTHER INFORMATION: MHC class I DLA-12 sequence

<400> SEQUENCE: 14

Asp Asp Ser Ala Gln Gly Ser Asp Val Ser Leu Thr Ala Pro Arg
1 5 10 15

<210> SEQ ID NO 15
<211> LENGTH: 12
<212> TYPE: PRT
<213> ORGANISM: Artificial Sequence
<220> FEATURE:
<223> OTHER INFORMATION: MHC class I DLA-12 sequence

<400> SEQUENCE: 15

Asn Tyr Leu Glu Thr Thr Cys Val Glu Trp Leu Arg
1 5 10

<210> SEQ ID NO 16
<211> LENGTH: 13
<212> TYPE: PRT
<213> ORGANISM: Artificial Sequence
<220> FEATURE:
<223> OTHER INFORMATION: MHC class I DLA-12 sequence

<400> SEQUENCE: 16

Ser Trp Thr Ala Ala Asp Ala Ala Ala Gln Ile Thr Arg
1 5 10

<210> SEQ ID NO 17
<211> LENGTH: 9
<212> TYPE: PRT
<213> ORGANISM: Artificial Sequence
<220> FEATURE:
<223> OTHER INFORMATION: MHC class I DLA-12 sequence

<400> SEQUENCE: 17

Gly Pro Gly Tyr Ser His Ala Ala Arg
1 5

<210> SEQ ID NO 18
<211> LENGTH: 9
<212> TYPE: PRT
<213> ORGANISM: Artificial Sequence
<220> FEATURE:
<223> OTHER INFORMATION: MHC class I DLA-12 sequence

<400> SEQUENCE: 18

Phe Asp Ser Asp Ala Ala Thr Gly Arg
1 5

<210> SEQ ID NO 19
<211> LENGTH: 10
<212> TYPE: PRT
<213> ORGANISM: Artificial Sequence
<220> FEATURE:
<223> OTHER INFORMATION: MHC class I DLA-12 sequence

<400> SEQUENCE: 19

Glu Ala Ala Gly Asp Ala Gly His Leu Arg
1 5 10

<210> SEQ ID NO 20
<211> LENGTH: 24
<212> TYPE: PRT
<213> ORGANISM: Artificial Sequence
<220> FEATURE:
<223> OTHER INFORMATION: MHC class I DLA-12 sequence

<400> SEQUENCE: 20

Asp Gly Glu Asp Gln Thr Gln Asp Thr Glu Val Val Asp Thr Arg Pro
1               5                   10                  15

Ala Gly Asp Gly Thr Phe Gln Lys
            20

<210> SEQ ID NO 21
<211> LENGTH: 11
<212> TYPE: PRT
<213> ORGANISM: Artificial Sequence
<220> FEATURE:
<223> OTHER INFORMATION: MHC class I DLA-12 sequence

<400> SEQUENCE: 21

His Pro Val Ser Asp His Glu Val Thr Leu Arg
1               5                   10

<210> SEQ ID NO 22
<211> LENGTH: 17
<212> TYPE: PRT
<213> ORGANISM: Artificial Sequence
<220> FEATURE:
<223> OTHER INFORMATION: MHC class I DLA-12 sequence

<400> SEQUENCE: 22

Ala Pro Trp Val Glu Gln Glu Gly Pro Glu Tyr Trp Asp Pro Gln Thr
1               5                   10                  15

Arg

<210> SEQ ID NO 23
<211> LENGTH: 15
<212> TYPE: PRT
<213> ORGANISM: Artificial Sequence
<220> FEATURE:
<223> OTHER INFORMATION: MHC class I DLA-12 sequence

<400> SEQUENCE: 23

Asp Asp Ser Ala Gln Gly Ser Asp Val Ser Leu Thr Ala Pro Arg
1               5                   10                  15

<210> SEQ ID NO 24
<211> LENGTH: 13
<212> TYPE: PRT
<213> ORGANISM: Artificial Sequence
<220> FEATURE:
<223> OTHER INFORMATION: MHC class I DLA-12 sequence

<400> SEQUENCE: 24

Trp Ala Ala Val Val Val Pro Ser Gly Gln Glu Gln Arg
1               5                   10

<210> SEQ ID NO 25
<211> LENGTH: 20
<212> TYPE: PRT
<213> ORGANISM: Artificial Sequence
<220> FEATURE:
<223> OTHER INFORMATION: MHC class I DLA-12 sequence

<400> SEQUENCE: 25

Gly Tyr Ser Gln Asp Ala Tyr Asp Gly Ala Asp Tyr Ile Ala Leu Asn
1               5                   10                  15

Glu Asp Leu Arg

20

<210> SEQ ID NO 26
<211> LENGTH: 12
<212> TYPE: PRT
<213> ORGANISM: Artificial Sequence
<220> FEATURE:
<223> OTHER INFORMATION: MHC class I DLA-12 sequence

<400> SEQUENCE: 26

Asn Tyr Leu Glu Thr Thr Cys Val Glu Trp Leu Arg
1 5 10

<210> SEQ ID NO 27
<211> LENGTH: 13
<212> TYPE: PRT
<213> ORGANISM: Artificial Sequence
<220> FEATURE:
<223> OTHER INFORMATION: MHC class I DLA-12 sequence

<400> SEQUENCE: 27

Ser Trp Thr Ala Ala Asp Ala Ala Ala Gln Ile Thr Arg
1 5 10

<210> SEQ ID NO 28
<211> LENGTH: 9
<212> TYPE: PRT
<213> ORGANISM: Artificial Sequence
<220> FEATURE:
<223> OTHER INFORMATION: MHC class I DLA-12 sequence

<400> SEQUENCE: 28

Gly Pro Gly Tyr Ser His Ala Ala Arg
1 5

<210> SEQ ID NO 29
<211> LENGTH: 9
<212> TYPE: PRT
<213> ORGANISM: Artificial Sequence
<220> FEATURE:
<223> OTHER INFORMATION: MHC class I DLA-12 sequence

<400> SEQUENCE: 29

Phe Asp Ser Asp Ala Ala Thr Gly Arg
1 5

<210> SEQ ID NO 30
<211> LENGTH: 14
<212> TYPE: PRT
<213> ORGANISM: Artificial Sequence
<220> FEATURE:
<223> OTHER INFORMATION: MHC class I DLA-12 sequence

<400> SEQUENCE: 30

Phe Ile Ala Val Gly Tyr Val Asp Asp Thr Gln Phe Val Arg
1 5 10

<210> SEQ ID NO 31
<211> LENGTH: 10
<212> TYPE: PRT
<213> ORGANISM: Artificial Sequence
<220> FEATURE:
<223> OTHER INFORMATION: MHC class I DLA-12 sequence

<400> SEQUENCE: 31

Glu Ala Ala Gly Asp Ala Gly His Leu Arg
1 5 10

-continued

<210> SEQ ID NO 32
<211> LENGTH: 7
<212> TYPE: PRT
<213> ORGANISM: Artificial Sequence
<220> FEATURE:
<223> OTHER INFORMATION: MHC class I DLA-12 sequence

<400> SEQUENCE: 32

Val Asp Leu Asp Thr Leu Arg
1               5

<210> SEQ ID NO 33
<211> LENGTH: 6
<212> TYPE: PRT
<213> ORGANISM: Artificial Sequence
<220> FEATURE:
<223> OTHER INFORMATION: MHC class I DLA-12 sequence

<400> SEQUENCE: 33

Tyr Leu Glu Met Gly Lys
1               5

<210> SEQ ID NO 34
<211> LENGTH: 354
<212> TYPE: DNA
<213> ORGANISM: Artificial Sequence
<220> FEATURE:
<223> OTHER INFORMATION: VH

<400> SEQUENCE: 34
gaggtccagc tgcagcagtc aggacctgag ctggtgaaac ctggggcctc agtgaagata     60
tcctgcaagg cttctggata cacattcact gactacaaca tgcactgggt gaaacagagc    120
catggaaaga gccttgagtg gattggatat atttatcctt acaatggtgg tactgactac    180
aaccagaaat tcaagagcaa ggccactttg actgtagaca attcctccag cacagcctac    240
atggagctcc gcagcctgac atctgatgac tctacagtct attactgtgc aagagggggc    300
ctagtcggtg ctatggacta ctggggccaa gggacctcgg tcaccgtctc ctca          354

<210> SEQ ID NO 35
<211> LENGTH: 321
<212> TYPE: DNA
<213> ORGANISM: Artificial Sequence
<220> FEATURE:
<223> OTHER INFORMATION: VL

<400> SEQUENCE: 35
gacattgaga tgacccagtc tccagcctcc ctttctgcat ctgtgggaga aactgtcacc     60
atcacatgtc gagcaagtgg gaatattcac aattctttag catggtatca gcagaaacag    120
ggaaaatctc ctcagctcct ggtctataat gcaaaaacct taccagatgg tgtgccatca    180
aggttcagtg gcagtggatc aggaacacaa tattctctca agatcaacag cctgcagcct    240
gaagattttg ggagttatta ctgtcaacat ttttggagta ttccgtggac gttcggtgga    300
gggaccaagc tggaaataaa a                                              321